United States Patent [19]

Kramer et al.

[11] Patent Number: 5,530,195
[45] Date of Patent: Jun. 25, 1996

[54] BACILLUS THURINGIENSIS GENE ENCODING A TOXIN ACTIVE AGAINST INSECTS

[75] Inventors: Vance C. Kramer, Hillsborough; Thomas C. Currier, Chapel Hill, both of N.C.

[73] Assignee: Ciba-Geigy Corporation, Tarrytown, N.Y.

[21] Appl. No.: 257,999

[22] Filed: Jun. 10, 1994

[51] Int. Cl.$^6$ .................. C07K 14/325; A01H 4/00; C12N 15/32; C12N 15/82

[52] U.S. Cl. ............... 800/205; 536/23.71; 435/252.3; 435/252.31; 435/252.34; 435/235.1; 435/69.1; 435/320.1; 424/93.2; 800/DIG. 56; 514/12; 530/350

[58] Field of Search .................. 536/23.71; 435/252.3, 435/252.31, 252.34, 235.1, 69.1, 320.1; 424/93.2; 800/205, DIG. 56; 514/12; 530/350

[56] References Cited

U.S. PATENT DOCUMENTS 5,045,469  9/1991  Payne et al. ................ 435/252.3
5,143,905  9/1992  Vasubramanian et al. ........ 514/12

OTHER PUBLICATIONS

Ge et al., "Location of the *Bombyx mori* specificity domain on a *Bacillus thuringiensis* δ-endotoxin protein", *Proc. Natl. Acad. Sci. USA*, 86:4037–4041 (1989).

Feitelson, "GenBank/EMBL Sequence Database, Accession No. M73253, cryIE(b) gene" (1991).

Hofte et al., "Insecticidal Crystal Proteins of *Bacillus thuringiensis*", *Microbiological Reviews*, 53(2):242–255 (1989).

Li et al., "Crystal structure of insecticidal δ-endotoxin from *Bacillus thuringiensis* at 2.5 Å resolution", *Nature*, 353:815–821 (1991).

Schnepf et al., "Specificity–determining Regions of a Lepidopteran-specific Insecticidal Protein Produced by *Bacillus thuringiensis*", *The Journal of Biological Chemistry*, 265(34):20923–20930 (1990).

Visser et al., "A Novel *Bacillus thuringiensis* Gene Encoding a *Spodoptera exigua*–Specific Crystal Protein", *Journal of Bacteriology*, 172(12):6783–6788 (1990).

Schnepf, et al (1990) Journal Biol. Chem. 265 (34):20923–20930.

Murray, et al (1991) Plant Molecular Biology 16: 1035, Abstract.

*Primary Examiner*—Che S. Chereskin
*Attorney, Agent, or Firm*—James Scott Elmer

[57] ABSTRACT

The present invention is drawn to a novel toxin gene purified and isolated from *Bacillus thuringiensis* var *kurstaki* and given the designation CryIE(c). The novel toxin gene encodes a protein of approximately 130 kDa in size and is active against Lepidopteran insects. Also included in the invention are the proteins encoded by CryIE(c). Further disclosed are recombinant genes and proteins derived from CryIE(c). Also provided are biologically pure bacterial strains transformed with the CryIE(c) gene which can be used in entomocidal formulations for the control of Lepidopteran insects. Yet another aspect of the invention are plants transformed with the toxin gene or active fragments thereof, particularly where the transforming sequences have been optimized for expression in maize.

20 Claims, 1 Drawing Sheet

BACILLUS THURINGIENSIS GENE ENCODING A TOXIN ACTIVE AGAINST INSECTS

FIELD OF THE INVENTION

The present invention relates to a novel toxin gene isolated from *Bacillus thuringiensis* var.*kurstaki*, to the protein encoded by the gene, recombinant strains comprising the gene and entomocidal compositions containing the recombinant strain, as well as transgenic plants comprising the novel toxin gene or its derivatives.

BACKGROUND OF THE INVENTION

*Bacillus thuringiensis* belongs to the large group of gram-positive, aerobic, endospore-forming bacteria. Unlike other very closely related species of *Bacillus* such as *B. cereus* or *B. anthracis*, the majority of the hitherto known *Bacillus thuringiensis* species produce in the course of their sporulation a parasporal inclusion body which, on account of its crystalline structure, is generally referred to also as a crystalline body. This crystalline body is composed of insecticidally active crystalline protoxin proteins, the so-called δ-endotoxins.

These protein crystals are responsible for the toxicity to insects of *Bacillus thuringiensis*. The δ-endotoxin does not exhibit its insecticidal activity until after oral intake of the crystalline body, when the latter is dissolved in the intestinal juice of the target insects. In most cases the actual toxic component is released from the protoxin as a result of proteolytic cleavage caused by the action of proteases from the digestive tract of the insects.

The δ-endotoxins of the various *Bacillus thuringiensis* strains are characterized by high specificity with respect to certain target insects, especially with respect to various Lepidoptera, Coleoptera and Diptera larvae, and by a high degree of activity against these larvae. A further advantage in using δ-endotoxins of *Bacillus thuringiensis* resides in the fact that the toxins are harmless to humans, other mammals, birds and fish.

With the introduction of genetic engineering and the new possibilities resulting from it, the field of *Bacillus thuringiensis* toxins has received a fresh impetus. For example, it is known that many naturally-occurring strains possess more than one insect toxin protein, which may account for a wide spectrum of insecticidal activity of those strains. However, with the ability to genetically transform *Bacillus* it is possible to create recombinant strains which may contain a chosen array of insect toxin genes obtained by isolation and cloning from naturally-occurring sources. Such recombinant strains can be made to provide whatever spectrum of insecticidal activity might be desired for a particular application, based upon a knowledge of the insecticidal activity of individual toxin proteins. Furthermore, it is also possible to create recombinant toxin proteins which have a chosen combination of functions designed to enhance the degree of insecticidal activity against a particular insect or insect class, or to expand the spectrum of insects against which the toxin protein is active.

The various insecticidal crystal proteins from *Bacillus thuringiensis* have been classified based upon their spectrum of activity and sequence similarity. The classification put forth by Höfte and Whiteley, Microbiol. Rev. 53:242–255 (1989) placed the then known insecticidal crystal proteins into four major classes. Generally, the major classes are defined by the spectrum of activity, with the CryI proteins active against Lepidoptera, CryII proteins active against both Lepidoptera and Diptera, CryIII proteins active against Coleoptera, and CryIV proteins active against Diptera.

Within each major class, the δ-endotoxins are grouped according to sequence similarity. The CryI proteins are typically produced as 130–140 kDa protoxin proteins which are proteolytically cleaved to produce active toxin proteins about 60–70 kDa. The active portion of the δ-endotoxin resides in the $NH_2$-terminal portion of the full-length molecule. Höfte and Whiteley, supra, classified the then known CryI proteins into six groups, IA(a), IA(b), IA(c), IB, IC, and ID. Since then, proteins classified as CryIE, CryIF, CryIG, and CryIX have also been characterized.

The spectrum of insecticidal activity of an individual δ-endotoxin from *Bacillus thuringiensis* tends to be quite narrow, with a given δ-endotoxin being active against only a few insects. Specificity is the result of the efficiency of the various steps involved in producing an active toxin protein and its subsequent ability to interact with the epithelial cells in the insect digestive tract.

To be insecticidal, a δendotoxin must first be ingested by the insect, solubilized and in most cases proteolytically cleaved to form an active toxin. Once activated, the δendotoxins bind to specific proteins present on the surface of the insect's gut epithelial cells through the agency of a specific domain on the protein toxin. In all cases examined, binding of the protein toxin to the insect gut occurs whenever there is toxicity. After binding, a different domain of the δendotoxin is thought to insert itself into the cell membrane creating a pore that results in the osmotic rupture of the insect's gut epithelial cell. The protein toxin's specificity to particular insects is thought to be determined, in large part, by the properties of the binding domain of an activated δendotoxin.

The size of the region of a δendotoxin required for binding to the insect gut cell binding protein is unclear. Schnepf et al. (J. Biol. Chem. 265: 20923–20930, 1990) have shown that the region between amino acids 332 and 722 contributes substantially to the specificity of CryIA(c) toward *Heliothis virescens* and that there are sub-sequences within this region which additively contribute to this specificity. This region of amino acids 332 to 722 spans both the specificity determining "Domain II" and the structural orientation determining "Domain III" as defined by Li et al. (Nature 353: 815–821, 1991). The importance of sub-sequences within this broad region is further emphasized by the findings of Ge et al. (Proc. Natl. Acad. Sci. USA, 74: 5463–5467, 1989), who identified a region of CryIA(a) from amino acids 332 to 450 that determined the specificity of the protein's toxicity toward the silkworm (*Bombyx mori*; Lepidoptera).

SUMMARY OF THE INVENTION

Figure 1:
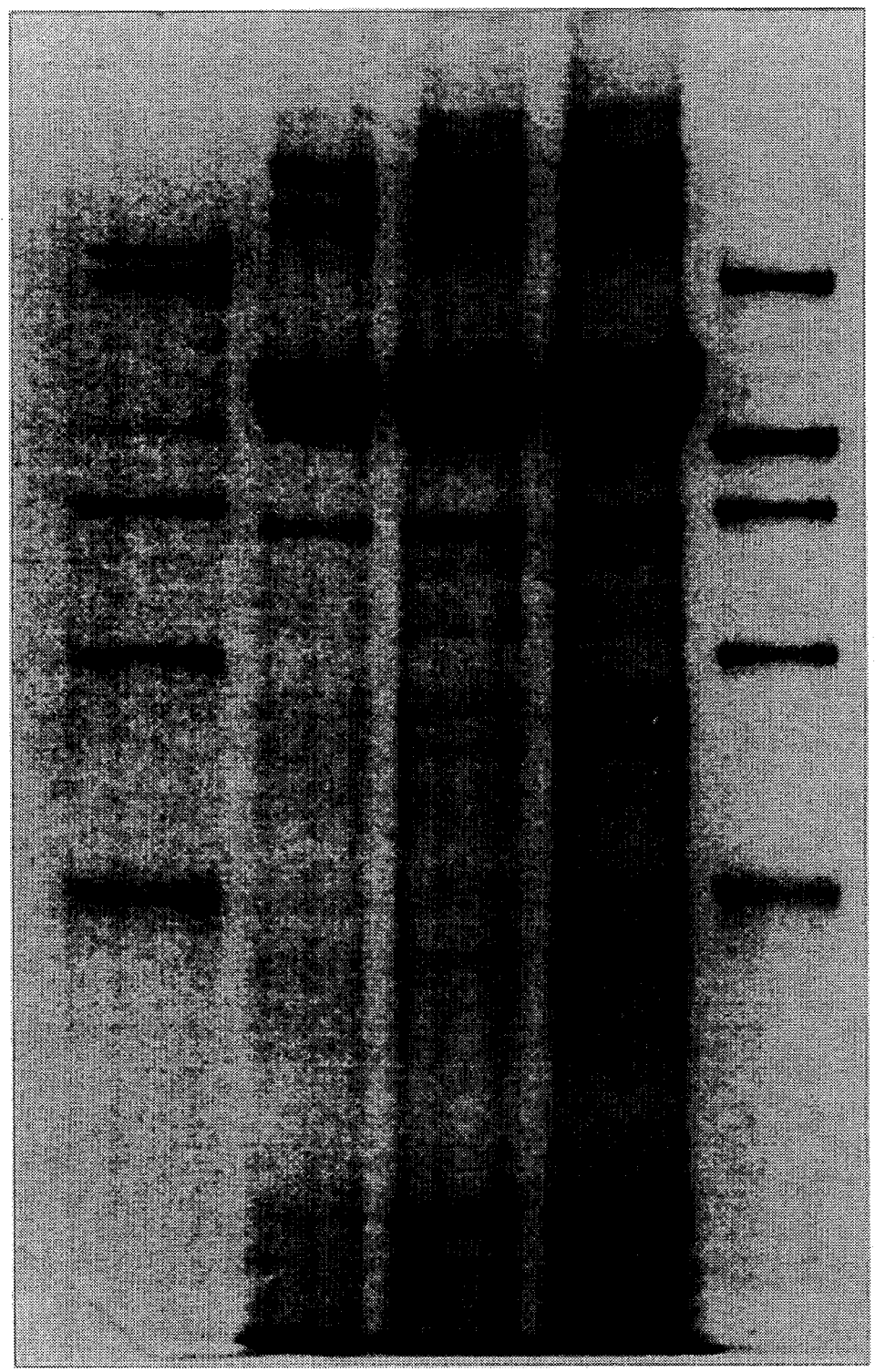
FIG. 1: SDS-PAGE analysis of the CryIE(c) protein expressed in the recombinant *Bacillus thuringiensis* strain CGB311.

The present invention is drawn to a novel toxin gene purified and isolated from *Bacillus thuringiensis* var *kurstaki*. The novel toxin gene encodes a protein of approximately 130 kDa in size and is active against Lepidopteran insects. The novel gene has been given the designation CryIE(c) (SEQ ID NO:1). Also included in the invention is the protein (SEQ ID NO:2) produced by CryIE(c). The invention further encompasses recombinant genes and proteins possessing one or more of the sub-sequences which confer activity against insects of the genus *Heliothis*. An additional aspect of the invention are recombinant, biologically pure microbial strains transformed with the CryIE(c) gene which can be used in entomocidal formulations for the control of Lepidopteran insects. Yet another aspect of the invention are plants transformed with the toxin gene or active fragments thereof, particularly where the transforming sequences have been optimized for expression in maize.

DETAILED DESCRIPTION OF THE INVENTION

The isolation and purification of the novel toxin gene of the present invention is described at length in Example 1. The coding region of the novel toxin gene (SEQ ID NO:1) extends from nucleotide base position 196 to position 3723. The protein produced by the novel toxin gene has the amino acid sequence disclosed as SEQ ID NO:2, and is further characterized in Example 5. According to the nomenclature scheme of Höfte and Whiteley, Microbiol. Rev. 53:242–255 (1989), the protein encoded by the novel toxin gene would be classified as a CryIE-type, and is designated herein as CryIE(c). The size of the CryIE(c) protein (SEQ ID NO:2), as deduced from the DNA sequence of the CryIE(c) gene (SEQ ID NO:1), is 130.7 kDa. This is similar in size to other known CryIE-type proteins. Despite the apparent size similarity, comparison of the amino acid sequence of the CryIE(c) protein (SEQ ID NO:2) with that of the previously reported CryIE-type protein shows significant differences between the two. The CryIE(c) protein (SEQ ID NO:2) has only 81% similarity to CryIE(a) protein and only 83% similarity to the CryIE(b) protein.

A comparison of the nucleotide base sequence of the CryIE(c) gene of the present invention with the corresponding coding regions of other CryIE-type genes known in the art indicate significant differences between them. The CryIE(c) gene of the present invention has only 87% sequence identity to the known endotoxin gene designated CryIE(a) and only 85% sequence identity to the known endotoxin gene designated CryIE(b).

While the CryIE(c) protein of the present invention shows limited sequence similarity with other known CryIE-type proteins, it exhibits insecticidal activity distinct from that of the known CryIE-type proteins. As shown below in Example 4, the protein encoded by the novel toxin gene of the present invention is active against the Lepidopteran insect *Heliothis virescens*. The CryIE-type proteins of the prior art are not known to be active against this insect pest. Furthermore, the CryIE-type proteins of the prior art are known to be active against the Lepidopteran insect *Spodoptera exigua* whereas the CryIE(c) protein of the present invention does not possess this activity.

The unique insecticidal activity of the CryIE(c) protein of the present invention against *Heliothis virescens* is the result of two sub-sequences located in the region spanning amino acid residues 332 to 622 of the protein. This region corresponds to regions identified in other δendotoxin proteins as responsible for insect specificity ("Domain II") and structural orientation ("Domain III"). See Li et al. (Nature 353:815–821, 1991). Sub-sequences within this region can be specified as corresponding to the domains described by Li et al., supra.

The first sub-sequence identified, Sub-Sequence A (SEQ ID NO:3), spans the region from amino acids 332 to 465. It is characterized as having low sequence similarity to other CryI-type toxin proteins yet is suggested to additively determine activity against *Heliothis virescens* based on the work of Schnepf et al., (J. Biol. Chem. 265: 20923–20930, 1990). Sub-Sequence A also corresponds to the specificity determining "Domain II" as described by Li et al., (Nature 353: 815–821, 1991).

The second sub-sequence identified, Sub-Sequence B (SEQ ID NO:4), spans the region from amino acids 466 to 622. This region is characterized by its high sequence similarity with the corresponding region found in another protein from *Bacillus thuringiensis*, CryIA(a), which is as active on *Heliothis virescens* as the novel toxin protein CryIE(c). The similarity between Sub-Sequence B and the corresponding region in CryIA(a) for the two proteins is shown in Table 1, below.

TABLE 1

Alignment of regions corresponding to Sub-Sequence B from CryIE(c) of the present invention and CryIA(a).

```
CryIE(c)  466  . . . . I T Q I P L V K A F N L H S G A T V A R G P G F T G G D I L R R T N V G N F G D M R V N I T  511
               | | | | |   |   | |   | |       |   : | | | | | | | | | | | | |   | : : :   | | | |
CryIA(a)  466  P S S Q I T Q I P L T K S T N L G S G T S V V K G P G F T G G D I L R R T S P G Q I S T L R V N I T  515

512  A P L S Q R Y R V R I R Y A S T T N L R F H T S I N G R A I N Q A D F P A T M N S G G N L Q S G S F  561
               | | | | | | | | | | | | | | | | | | . | | | | | : | | : | | | : : . | | | . | | : | | | | | |
          516  A P L S Q R Y R V R I R Y A S T T N L Q F H T S I D G R P I N Q G N F S A T M S S G S N L Q S G S F  565

562  R I A G F T T P F T F S D A L S T F T I G A F G F S S G N E V Y I D R I E F V P A E V T F E A E Y D  611
               | . . | | | | | | . | | : :   | . | | : : |   . | . | | | | | | | | | | | | | | | | | | | | | |
          566  R T V G F T T P F N F S N G S S V F T L S A H V F N S G N E V Y I D R I E F V P A E V T F E A E Y D  615

612  L E R A Q K A V N A L  622
               | | | | | | |
          616  L E R A Q K A . . . .  622
```

Percent Similarity: 86 Percent Identity: 77.
Similarities and identities were done using the GAP program from UWGCG.

The high percent similarity (86%) between the Sub-Sequence B region of the novel toxin protein CryIE(c) of the present invention and the corresponding region of the CryIA(a) protein indicates the conserved nature of the region which confers toxicity to *Heliothis virescens*. When Sub-Sequence B of the novel toxin protein CryIE(c) of the present invention is compared with the corresponding region for the related protein CryIE(a), which is not active against *Heliothis virescens*, it is found that the percent similarity is only 63%.

The present invention is intended to cover mutants and recombinant or genetically engineered derivatives of the CryIE(c) gene (SEQ ID NO:1). For example, it is well known that CryI-type proteins must be proteolytically cleaved into a toxic core fragment that is the actual toxic molecule. Hence, a truncated DNA sequence which encodes for the toxic core fragment of the novel toxin protein CryIE(c) is considered to be within the scope of the present invention. In addition, a recombinant toxin protein may be constructed using methods known in the art which contain one or both of the sub-sequences conferring activity against *Heliothis virescens* (SEQ ID NOS:3 to 4). Such a recombinant protein would have activity against *Heliothis virescens*, in addition to its native properties. Mutants of the CryIE(c) gene of the present invention are also encompassed by the present invention. For example, individual nucleotides may be altered, either by natural processes or by site-directed mutagenesis, which in turn creates a change in the amino acid sequence of the encoded protein. In addition, the DNA sequence of either the full-length or truncated form of the gene may be altered such that its expression is optimized for plants, where the codons are chosen so as to produce a protein having the same or similar amino acid sequence as that encoded by the native form of the CryIE(c) gene. Other modifications of the novel toxin gene that yield a protein with insecticidal properties essentially the same as those of the CryIE(c) protein (SEQ ID NO:2) are also encompassed by the present invention.

The CryIE(c) gene (SEQ ID NO:1), or the sub-sequences of the gene which confer specificity against *Heliothis virescens*, are also useful as a DNA hybridization probe, for discovering similar or closely related cryI-type or genes active against *Heliothis virescens* in other *Bacillus thuringiensis* strains. The cryIE(c) gene (SEQ ID NO:1), or portions or derivatives thereof, can be labeled for use as a hybridization probe, e.g., with a radioactive label, using conventional procedures. The labeled DNA hybridization probe may then be used in the manner described in the Example 1.

Recombinant Microorganisms Comprising the Novel Toxin Gene and Protein

The utility of the novel toxin gene present in a recombinant strain of *Bacillus thuringiensis* is illustrated in Examples 3 to 4. It should also be recognized that the isolated novel toxin gene of the present invention can be transferred into any microbial host and confer its insecticidal properties upon that host. Alternate hosts for the novel toxin gene of the present invention can be selected as suitable for cloning purposes, for purposes of characterizing the form and function of the gene or encoded protein, for use as a fermentation host to increase production of the toxin protein, for purposes of delivering the toxin protein more effectively to the target insect pest, or introduction of the novel toxin gene into insect pathogens such as baculovirus to improve their effectiveness.

The novel toxin gene or recombinant forms thereof can be transformed into such alternate hosts using a variety of art recognized methods. One such preferred method is electroporation of microbial cells, as described, for example, by the method of Dower (U.S. Pat. No. 5,186,800). Another preferred method is that of Schurter et al. (Mol. Gen. Genet. 218:177–181 (1989)), which is also disclosed in U.S. Ser. No. 07/353,565 which is incorporated herein in its entirety.

It is envisioned that said alternate host would be applied to the environment or plants or animals for insect control. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., *Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes,* fungi, particularly yeast, e.g., *Saccharomyces, Cryptococcus, Kluyveromyces, Sporobolomyces, Rhodotorula,* and *Aureobasidium.* Of particular interest are such phytosphere bacterial species as *Bacillus* spp., *Pseudomonas syringae, Pseudomonas fluorescens, Serratia marcescens, Acetobacter xylinum, Agrobacteria, Rhodopseudomonas spheroides, Xanthomomonas campestris, Rhizobium melioti, Alcaligenes entrophus, Clavibacter xyli* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans.* Of particular interest are the pigmented microorganisms.

The present invention further provides an entomocidal composition comprising a recombinant *Bacillus thuringiensis* strain containing the novel toxin gene in recombinant form, or a derivative or mutant thereof, together with an agricultural adjuvant such as a carder, diluent, surfactant or application-promoting adjuvant. The composition may also contain a further biologically active compound selected from fertilizers, micronutrient donors, plant growth preparations, herbicides, insecticides, fungicides, bactericides, nematicides and molluscicides and mixtures thereof. The composition may comprise from 0.1 to 99% by weight of the recombinant *Bacillus thuringiensis* strain containing the novel gene in recombinant form, or the derivative or mutant thereof, from 1 to 99.9% by weight of a solid or liquid adjuvant, and from 0 to 25% by weight of a surfactant. The recombinant *Bacillus thuringiensis* strain containing the novel gene in recombinant form, or the composition containing it, may be administered to the plants or crops to be protected together with certain other insecticides or chemicals (1993 Crop Protection Chemicals Reference, Chemical and Pharmaceutical Press, Canada) without loss of potency. It is compatible with most other commonly used agricultural spray materials but should not be used in extremely alkaline spray solutions. It may be administered as a dust, a suspension, a wettable powder or in any other material form suitable for agricultural application.

Target crops to be protected within the scope of the present invention comprise, e.g., the following species of plants:

cereals (wheat, barley, rye, oats, rice, sorghum and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

Entomocidal Compositions Comprising a Recombinant Bacillus thuringiensis Strain

The recombinant Bacillus thuringiensis strain containing the novel gene in recombinant form is normally applied in the form of entomocidal compositions and can be applied to the crop area or plant to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The formulations, i.e. the entomocidal compositions, preparations or mixtures containing the recombinant *Bacillus thuringiensis* strain containing the novel gene in recombinant form as an active ingredient or combinations thereof with other active ingredients, and, where appropriate, a solid or liquid adjuvant, are prepared in known manner, e.g., by homogeneously mixing and/or grinding the active ingredients with extenders, e.g., solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carders used, e.g., for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carders are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds. Suitable soaps are the alkali metal salts, alkaline earth metal salts or unsubstituted or substituted ammonium salts of higher fatty acids (C sub 10 -C sub 22), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates. The fatty sulfonates or sulfates are usually in the forms of alkali metal salts, alkaline earth metal salts or unsubstituted or substituted ammonium salts and generally contain a C sub 8 -C sub 22 alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide. Non-ionic surfactant are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of nonionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one C sub 8 -C sub 22 alkyl radical and, as further substituents, lower unsubstituted or halogenated alkyl, benzyl or hydroxyl-lower alkyl radicals. The salts are preferably in the form of halides, methylsulfates or ethylsulfates, e.g., stearyltrimethylammonium chloride or benzyldi-(2-chloroethyl)ethylammonium bromide.

The surfactants customarily employed in the art of formulation are described, e.g., in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna.

Another particularly preferred characteristic of an entomocidal composition of the present invention is the persistence of the active ingredient when applied to plants and soil. Possible causes for loss of activity include inactivation by ultra-violet light, heat, leaf exudates and pH. For example, at high pH, particularly in the presence of reductant, δendotoxin crystals are solubilized and thus become more accessible to proteolytic inactivation. High leaf pH might also be important, particularly where the leaf surface can be in the range of pH 8–10. Formulation of an entomocidal composition of the present invention can address these problems by either including additives to help prevent loss of the active ingredient or encapsulating the material in such a way that the active ingredient is protected from inactivation. Encapsulation can be accomplished chemically (McGuire and Shasha, 1992) or biologically (Barnes and Cummings, 1986). Chemical encapsulation involves a process in which the active ingredient is coated with a polymer while biological encapsulation involves the expression of the δendotoxin genes in a microbe. For biological encapsulation, the intact microbe containing the δendotoxin protein is used as the active ingredient in the formulation. The addition of UV protectants might effectively reduce irradiation damage. Inactivation due to heat could also be controlled by including an appropriate additive.

The entomocidal compositions usually contain 0.1 to 99%, preferably 0.1 to 95%, of the recombinant *Bacillus thuringiensis* strain containing the novel gene in recombinant form, or combination thereof with other active ingredients, 1 to 99.9% of a solid or liquid adjuvant, and 0 to 25%, preferably 0.1 to 20%, of a surfactant. Whereas commercial products are preferably formulated as concentrates, the end user will normally employ dilute formulations of substantially lower concentration. The entomocidal compositions may also contain further ingredients, such as stabilizers, antifoams, viscosity regulators, binders, tackifiers as well as fertilizers or other active ingredients in order to obtain special effects.

Transgenic Plants Comprising the Novel Toxin Gene or Protein

A host plant expressing the novel toxin genes of the invention will have enhanced resistance to insect attack and will be thus better equipped to withstand crop losses associated with such attack.

It has been discovered that the codon usage of a native *Bacillus thuringiensis* toxin gene is significantly different from that which is typical of a plant gene. In particular, the codon usage of a native *Bacillus thuringiensis* gene is very different from that of a maize gene. As a result, the mRNA from this gene may not be efficiently utilized. Codon usage might influence the expression of genes at the level of translation or transcription or mRNA processing. To optimize a toxin gene for expression in plants, for example in maize, the codon usage is optimized by using the codons which are most preferred in maize (maize preferred codons) in the synthesis of a synthetic gene which encodes the same protein as found for the native toxin gene sequence. The optimized maize preferred codon usage is effective for expression of high levels of the Bt insecticidal protein. Further details for constructing maize-optimized synthetic toxin genes can be found in U.S. Ser. No. 07/951,175, herein incorporated by reference in its entirety.

Toxin genes derived from microorganisms may also differ from plant genes. Plant gene differ from genes found in microorganisms in that their transcribed RNA does not possess defined ribosome binding site sequence adjacent to the initiating methionine. Consequently, microbial genes can be enhanced by the inclusion of a eukaryotic consensus translation initiator at the ATG. Clontech (1993/1994 catalog, page 210) has suggested the sequence GTCGACCATG-GTC (SEQ ID NO:5) as a consensus translation initiator for the expression of the *E. coli uidA* gene in plants. Further, Joshi (NAR 15:6643–6653 (1987)) has compared many plant sequences adjacent to the ATG and suggests the consensus TAAACAATGGCT (SEQ ID NO:6). In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. By surveying the sequence of maize genes present in the GenBank/EMBL database it can be discerned which nucleotides adjacent to the ATG should be modified to enhance translation of the toxin gene introduced into maize.

In addition, it has been shown that removal of illegitimate splice sites can enhance expression and stability of introduced genes. Genes cloned from non-plant sources and not optimized for expression in plants may contain motifs which can be recognized in plants as 5' or 3' splice sites. Consequently, the transcription process can be prematurely terminated, generating truncated or deleted mRNA. The toxin genes can be engineered to remove these illegitimate splice sites using the techniques disclosed in U.S. Ser. No. 07/961,944, hereby incorporated by reference in its entirety.

It is well known that many δendotoxin proteins from *Bacillus thuringiensis* are actually expressed as protoxins. These protoxins are solubilized in the alkaline environment of the insect gut and are proteolytically converted by proteases into a toxic core fragment (Höfte and Whiteley, Microbiol. Rev. 53:242–255 (1989)). For δendotoxin proteins of the CryI class, the toxic core fragment is localized in the N-terminal half of the protoxin. It is within the scope of the present invention that genes encoding either the full-length protoxin form or the truncated toxic core fragment of the novel toxin protein can be used in plant transformation vectors to confer insecticidal properties upon the host plant.

The recombinant DNA molecules can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., BioTechniques 4:320–334 (1986)), electroporation (Riggs et al, Proc. Natl. Acad. Sci. USA 83:5602–5606 (1986), Agrobacterium-mediated transformation (Hinchee et at., Biotechnology 6:915–921 (1988)), direct gene transfer (Paszkowski et at., EMBO J. 3:2717–2722 (1984)), and ballistic particle acceleration using devices available from Agracetus, Inc., Madison, Wisconsin and Dupont, Inc., Wilmington, Del. (see, for example, Sanford et al., U.S. Pat. No. 4,945,050; and McCabe et al., Biotechnology 6:923–926 (1988)). Also see, Weissinger et al., Annual Rev. Genet. 22:421–477 (1988); Sanford et al., Particulate Science and Technology 5:27–37 91987)(onion); Christou et al., Plant Physiol. 87:671–674 (1988)(soybean); McCabe et al., Bio/Technology 6:923–926 (1988)(soybean); Datta et al., Bio/Technology 8:736–740 (1990)(rice); Klein et al., Proc. Natl. Acad. Sci. USA, 85:4305–4309 (1988)(maize); Klein et al., Bio/Technology 6:559–563 (1988)(maize); Klein et al., Plant Physiol. 91:440–444 (1988)(maize); Fromm et al., Bio/Technology 8:833–839 (1990); and Gordon-Kamm et al., Plant Cell 2:603–618 (1990)(maize); Svab et al. Proc. Natl. Acad. Sci. USA 87:8526–8530 (1990) (tobacco chloroplast); Koziel et al. (Biotechnology 11:194–200 (1993)) (maize); Shimamoto et al. Nature 338:274–277 (1989)(rice); Christou et al. Biotechnology 9:957–962 (1991)(rice); European Patent Application EP 0 332 581 (orchardgrass and other *Pooideae*); Vasil et al. (Biotechnology 11:1553–1558 (1993) (wheat); Weeks et al. (Plant Physiol. 102:1077–1084 (1993) (wheat).

One particularly preferred set of embodiments for the introduction of recombinant DNA molecules into maize by microprojectile bombardment can be found in U.S. Ser. No. 08/008,374, herein incorporated by reference in its entirety. An additional preferred embodiment is the protoplast transformation method for maize as disclosed in European Patent Application EP 0 292 435, as well as in U.S. Ser. No. 08/024,875, hereby incorporated by reference in its entirety.

Transformation of plants can be undertaken with a single DNA species or multiple DNA species (i.e. co-transformation) and both these techniques are suitable for use with the novel toxin gene of the present invention.

Methods using either a form of direct gene transfer or *Agrobacterium*-mediated transfer usually, but not necessarily, are undertaken with a selectable marker which may provide resistance to an antibiotic (kanamycin, hygromycin or methotrexate) or a herbicide (phosphinothricin). The choice of selectable marker for plant transformation is not, however, critical to the invention.

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the *nptII* gene which coffers resistance to kanamycin and related antibiotics (Messing & Vierra, Gene 19:259–268 (1982); Bevan et al., Nature 304:184–187 (1983)), the bar gene which coffers resistance to the herbicide phosphinothricin (White et al., Nucl Acids Res 18:1062 (1990), Spencer et al. Theor Appl Genet 79:625–631 (1990)), the *hph* gene which confers resistance to the antibiotic hygromycin (Blochinger & Diggelmann, Mol Cell Biol 4:2929–2931), and the *dhfr* gene, which confers resistance to methotrexate (Bourouis et al., EMBO J. 2:1099–1104 (1983).

Many vectors are available for transformation using *Agrobacterium tumefaciens*. These typically carry at least one T-DNA border sequence and include vectors such as pBIN19 (Bevan, Nucl. Acids Res. (1984)). In one preferred embodiment, the novel toxin gene of the present invention may be inserted into either of the binary vectors pCIB200 and pCIB2001 for use with *Agrobacterium*. These vector cassettes for Agrobacterium-mediated transformation can be constructed in the following manner. pTJS75kan was created by *NarI* digestion of pTJS75 (Schmidhauser & Helinski, J Bacteriol. 164:446–455 (1985)) allowing excision of the tetracycline-resistance gene, followed by insertion of an *AccI* fragment from pUC4K carrying an NPTII (Messing & Vierra, Gene 19:259–268 (1982); Bevan et al., Nature 304:184–187 (1983); McBride et al., Plant Molecular Biology 14:266–276 (1990)). *XhoI* linkers were ligated to the *EcoRV* fragment of pCIB7 which contains the left and right T-DNA borders, a plant selectable *nos/nptII* chimetic gene and the pUC polylinker (Rothstein et al., Gene 53:153–161 (1987)), and the *XhoI*-digested fragment was cloned into *SalI*-digested pTJS75kan to create pCIB200 (see also EP 0 332 104, example 19). pCIB200 contains the following unique polylinker restriction sites: *EcoRI, SstI, KpnI, BglII, XbaI,* and *SalI*. pCIB2001 is a derivative of pCIB200 which created by the insertion into the polylinker of additional restriction sites. Unique restriction sites in the polylinker of pCIB2001 are *EcoRI, SstI, KpnI, BglII, XbaI, SalI, MluI, BclI, AvrII, ApaI, HpaI,* and *StuI*. pCIB2001, in addition to containing these unique restriction sites also has plant and bacterial kanamycin selection, left and right T-DNA borders for *Agrobacterium*-mediated transformation, the RK2-derived *trfA* function for mobilization between *E. coli* and other hosts, and the *OriT* and *OriV* functions also from RK2. The pCIB2001 polylinker is suitable for the cloning of plant expression cassettes containing their own regulatory signals.

An additional vector useful for *Agrobacterium*-mediated transformation is the binary vector pCIB10 contains a gene encoding kanamycin resistance for selection in plants, T-DNA right and left border sequences and incorporates sequences from the wide host-range plasmid pRK252 allowing it to replicate in both *E. coil* and *Agrobacterium*. Its construction is described by Rothstein et al. (Gene 53: 153–161 (1987)). Various derivatives of pCIB10 have been constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715,pCIB717).

Other transformation techniques which do not rely on *Agrobacterium*, the so-called direct gene transfer methods, are also useful for the introduction of the novel toxin gene of the present invention, including transformation by microprojectile bombardment, protoplast uptake (e.g. PEG and electroporation) and microinjection. The choice of vector for these methods depends largely on the preferred selection for the species being transformed.

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. The gene for resistance to phosphinothricin was obtained from the John Innes Centre, Norwich in pJIT82 which contains bar gene from *Streptomyces viridochromogenes* (Thompson et al. EMBO J 6:2519–2523 (1987)). This vector is suitable for the cloning of plant expression cassettes containing their own regulatory signals.

An additional transformation vector is pSOG35 which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the 6US untranslated leader sequence from pSOG 10. A 250 bp fragment encoding the *E. coli* dihydrofolate reductase type II gene was also amplified by PCR and these two PCR fragments were assembled with a *SacI-PstI* fragment from pBI221 (Clontech) which comprised the pUC 19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG 19 and pSOG35 carry the pUC gene for ampicillin resistance and have *HindIII, SphI, PstI* and *EcoRI* sites available for the cloning of foreign sequences.

The novel toxin genes of the present invention, either as their native sequence or as optimized synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. Preferred constitutive promoters include the CaMV 35S and 19S promoters. An additionally preferred promoter is derived from any one of several of the actin genes, which are known to be expressed in most cell types. The promoter expression cassettes described by McElroy et al. (Mol. Gen. Genet. 23 1:150–160 (1991)) can be easily modified for the expression of the novel toxin gene and are particularly suitable for use in monocotyledonous hosts.

Yet another preferred constitutive promoter is derived from ubiquitin, which is another gene product known to accumulate in many cell types. The ubiquitin promoter has been cloned from several species for use in transgenic plants (e.g. sunflower - Binet et al. Plant Science 79: 87–94 (1991), maize - Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin gene in plants, particularly maize, are those which direct expression in root, pith, leaf or pollen. Such promoters are disclosed in U.S. Ser. No. 07/951,715, herein incorporated by reference in its entirety. Chemically inducible promoters useful for directing the expression of the novel toxin gene in plants are disclosed in U.S. Ser. No. 08/181,271, herein incorporated by reference in its entirety.

In addition to promoters, a variety of transcriptional terminators are also available for use in chimeric gene construction using the novel toxin gene of the present invention. Transcriptional terminators are responsible for the termination of transcription beyond the transgene and its correct polyadenylation. Appropriate transcriptional terminators and those which are known to function in plants include the CaMV 35S terminator, the *tml* terminator, the nopaline synthase terminator, the pea *rbcS* E9 terminator and others known in the art. These can be used in both monocotyledons and dicotyledons.

Numerous sequences have also been found to enhance gene expression from within the transcriptional unit and these sequences can be used in conjunction with the novel toxin gene of this invention to increase their expression in transgenic plants.

Various intron sequences have been shown to enhance expression, particularly in monocotyledonous cells. For example, the introns of the maize *Adh*1 gene have been found to significantly enhance the expression of the wild-type gene under its cognate promoter when introduced into maize cells (Callis et al., Genes Develep 1:1183–1200 (1987)). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15:8693–8711 (1987); Skuzeski et al. Plant Molec. Biol. 15; 65–79 (1990))

EXAMPLES

The following examples further describe the materials and methods used in carrying out the invention and the subsequent results. They are offered by way of illustration, and their recitation should not be considered as a limitation of the claimed invention.

Example 1: Cloning and Isolation of the Novel Toxin Gene

Total DNA was isolated from *Bacillus thuringiensis* var *kurstaki* strain CGB316. A culture of CGB316 was grown overnight in L-broth at 25° C. with 150 rpm of shaking in a rotary shaker. The culture was then centrifuged, and resuspended in 8% sucrose, 100 mM Tris pH 8.0, 10 mM EDTA, 50 mM NaCl and 2 mg/ml lysozyme, and incubated for 30 minutes at 37° C. Fifty µg/ml proteinase K and SDS to a final concentration of 0.2% were then added and the resultant mixture incubated at 50° C. until the solution became very viscous. An equal volume of phenol/chloroform was added to the viscous mixture, vortexed and centrifuged to separate the aqueous and organic phases. The aqueous phase was then mixed with 1 g/ml CsCl and 150 µg/ml ethidium bromide, placed in an 33 ml Naigene UltraLok tube and centrifuged at 45,000 rpm for 16 hours in a Beckman Ti50 ultracentrifuge rotor. The resultant DNA band was visualized with a UV light source and was removed with a syringe using a 16 gauge needle. Contaminating ethidium bromide was removed from the DNA sample by isoamyl alcohol extraction. The isolated DNA was precipitated with 2 volumes 100% ethanol and centrifuged. The resulting DNA pellet was washed with 70% ethanol. The DNA pellet was dried and resuspended in 10 mM Tris pH 8.0, 1 mM EDTA.

Fifteen µg of isolated DNA from the CGB316 strain was digested with 0.1 units Sau3A/µg DNA at 37° C. At 3, 5 and 10 minutes after addition of restriction enzyme 5 µg samples were removed from the digest mixture, EDTA was added made to a final concentration of 10 mM and placed on ice. An aliquot of each timed digest was loaded on a 0.8% agarose gel utilizing a Tris-borate-EDTA (TBE; Molecular Cloning, A Laboratory Manual, Sambrook et al. eds. Cold Spring Harbor Press: New York (1989)) buffer and run overnight at 25 volts in an IBI model MPH gel electrophoresis system. Lambda DNA digested with HindIII was used as molecular weight markers for the gel run. After electrophoresis, DNA fragments in the 6–9 kb range were cut out of the gel. DNA was electroeluted out of the agarose gel slices by placing them in a Nanotrap electroelution trap and utilizing a ISCO Little Blue Tank with a buffer system and current using the procedure described by the supplier of the apparatus. After electroelution, the isolated DNA was precipitated by addition of 1/10 volume 3M sodium acetate pH 4.8, 2.5 volumes 100% ethanol and then centrifuged. The resulting DNA pellet was washed with 70% ethanol and centrifuged. The DNA pellet was dried and resuspended in 10 mM Tris pH 8.0, 1 mM EDTA.

Ligation into pUC19 of the isolated DNA fragments having sizes of 6–9 kb were done using 4 μl of the above DNA solution, 1 μl of a 100 ng/μl solution of pUC19 that was previously digested with Bam HI and treated with calf alkaline phosphatase, 1 μl 10X ligation buffer, 3 μl water and 1 μl containing 3 units T4 ligase. This mixture was incubated at 15° C. overnight. The resulting pUC19-based plasmids containing the inserted DNA fragments isolated from the *Bacillus thuringiensis* strain was transformed into *E. coli* DH5α competent cells. This was accomplished by combining the ligation mixture with 200 μl of bacterial cells, placement on ice for 1–2 hours and subsequent heating at 42° C. for 90 seconds. After treatment the bacterial solution was mixed with 200 μl of SOC medium (*Molecular Cloning, A Laboratory Manual*, Sambrook et al. eds. Cold Spring Harbor Press: New York (1989)), placed at 37° C. for 45 minutes and plated on L-agar plates containing 100 μg/ml ampicillin to select for transformants. The plates were incubated overnight at 37° C.

Transformed colonies arising after overnight incubation were subjected to the colony hybridization procedure as described in *Molecular Cloning, A Laboratory Manual*, Sambrook et al. eds. Cold Spring Harbor Press: New York (1989).

In brief, a 85 mm Nitroplus 2000 filter circle was placed on each agar plate containing transformed colonies and then lifted off. After removing the filter, the plates were again placed at 37° C. until transformed colonies were visible again. The filters with the colonies on them were treated to release DNA from the bacterial cells first on Whatman paper saturated with 10% SDS, then 0.5N NaOH-1.5M NaCl, then 1.5M NaCl-0.5M Tris pH 7.4 for 3 minutes each. The filters were then treated with 2X SSC and the released bacterial DNA was fixed to the filters by UV crosslinking using a Stratalinker (Stratagene) at 0.2 mJoule.

A total of 6 plates with 100–200 colonies/plate were done for the DNA fragments isolated from the CGB316 strain of *Bacillus thuringiensis*. Prehybridization and hybridization of the filter was carried out in a solution of 10X Denhardt's solution, 150 μg/ml sheared salmon sperm DNA, 1% SDS, 50 mM sodium phosphate pH 7, 5 mM EDTA, 6X SSC, 0.05% sodium pyrophosphate. Prehybridization was at 65° C. for 4 hours and hybridization was at 65° C. for 18 hrs with 1 million cpm/ml of a $^{32}$P-dCTP labeled probe in a volume of 50 ml. Radiolabeled DNA probes were prepared using a BRL random prime labeling system and unincorporated counts removed using Nick Columns (Pharmacia).

Filters were probed with a cryIB radiolabeled fragment generated by Polymerase Chain Reaction. The generated fragment spans the region from 461–1366 bp of the cryIB gene. Hybridization probes were boiled 5 minutes before addition to the hybridization solution. The filters were washed twice in 50 ml of 2X SSC, 0.5% SDS at 65° C. for 20 minutes. The probed and washed filters were exposed to Kodak X-Omat AR X-ray film with Dupont Cronex Lightning Plus intensifying screens at −80° C. Those colonies which were positive by hybridization were identified and picked from the regrown plates. Picked colonies were streaked on L-agar with 100 μg/ml ampicillin. Plasmid DNA was isolated from each streaked culture using the alkaline miniprep method described in *Molecular Cloning, A Laboratory Manual*, Sambrook et al. eds. Cold Spring Harbor Press: New York (1989).

One clone isolated was designated CGB316#A. It contained a recombinant plasmid which was shown by the above procedure to possess a DNA fragment isolated from *Bacillus thuringiensis* strain CGB316 which positively hybridized to the CryIB probe.

The DNA fragment isolated from the *Bacillus thuringiensis* strain and contained in the recombinant plasmid was re-cloned into pHT3101, a shuttle vector which allows plasmid manipulation in either *E. coli* or *Bacillus thuringiensis*. pHT3101 is composed of pUC 18, a Bt replicon and an erythromycin gene for selection in Bt (Lereclus et al 1992). The recombinant plasmid containing the cloned DNA from *Bacillus thuringiensis* was isolated from the *E. coli* cells using standard procedures (*Molecular Cloning, A Laboratory Manual*, Sambrook et al. eds. Cold Spring Harbor Press: New York (1989)). To remove the cloned *Bacillus thuringiensis* DNA from the recombinant plasmid, the isolated plasmid from the clone CGB316#A was digested with the restriction enzymes Sac I and Bbu I. The digestion mixtures were then loaded on a 1% SeaPlaque® agarose gel using TBE buffer system and electrophoresed overnight at 25 volts. After electrophoresis, a DNA fragment of approximately 7 kb in size was isolated from the gel using the above described procedures. The DNA fragment isolated from the gel was ligated into pHT3101 using the previously described procedure by combining 5 μl of the melted (65° C.) agarose fragment and 4 μl 10 ng/gl of pHT3101.

The approximately 7 kb fragment of *Bacillus thuringiensis* DNA isolated from the clone CGB316#A and ligated in pHT3101 was designated pCIB5618. The *E. coli* strain containing plasmid pCIB5618 was designated CGE5618. CGE5618 was deposited on Jun. 1, 1994 with the Agricultural Research Service, Patent Culture Collection (NRRL), Northern Regional Research Center, 1815 North University Street, Peoria, Ill. 61604, U.S.A. and was assigned accession number NRRL B-21275.

Example 2: DNA Sequence Analysis of Novel Toxin Gene and Homology of Deduced Protein Sequence to other CryI Genes The DNA sequence of the novel toxin gene of the present invention was obtained by first synthesizing sequencing primers using an Applied Biosystems model 380B DNA synthesizer. The primers were then used in the DNA sequencing reactions. Sequencing was performed using the dideoxy chain-termination method (Sanger et al. 1977). Sequencing reactions were carried out using the Sequenase system (US Biochemical Corp.) and gel analysis performed on 40 cm gels of 6% polyacrylamide with 7M urea in Tris-Borate-EDTA buffer (BRL Gel-Mix 6). Analysis of sequences was done using the University of Wisconsin Genetic Computer Group Sequence Analysis Software (UWGCG).

The complete nucleotide sequence of the isolated novel toxin gene is disclosed in SEQ ID NO:1 and the deduced amino acid sequence of the encoded protein is disclosed in SEQ ID NO:2. Using the FASTA program available in UWGCG, the DNA sequence of the novel toxin gene of the present invention has 87% sequence identity to the known endotoxin gene designated CryIE(a) (GenBank/EMBL Accession No. M73252) and 85% sequence identity to the known endotoxin gene CryIE(b) (GenBank/EMBL Accession No. M73252). The deduced protein sequence has 83% similarity to CryIE(b) and 81% similarity to CryIE(a). According the nomenclature scheme of Höfte and Whiteley, Microbiol. Rev. 53:242–255 (1989) the protein encoded by the novel toxin gene would be classified as a CryIE-type, and is designated herein as CryIE(c). The CryIE(c) gene of the present invention encodes a crystal protein of 1176 amino acids with a predicted molecular mass of 130.7 kDa.

Example 3: Transformation of *Bacillus thuringiensis* with Novel Toxin Genes The cloned gene for the novel toxin present in the recombinant plasmids pCIB5618 was transformed into the acrystalliferous derivative of *Bacillus thuringiensis* designated CGB315. Transformation was accomplished by the method of Schurter et al. (Mol. Gen. Genet. 218:177– 181 (1989)), which is also disclosed in U.S. Ser. No. 07/353,565 which is incorporated herein in its entirety.

Spores of CGB315 are inoculated into 10 ml of L-broth and incubated overnight at 25° C. on a rotary shaker at 100 rpm. After incubation, the culture is diluted 50-fold into L-broth and incubated further at 30° C. on a rotary shaker at 250 rpm until the culture reaches an $OD_{550}$ of 0.2. The bacterial cells are harvested by centrifugation and resuspended in 1/40 volume ice-cold electroporation buffer (400 mM sucrose, 1 mM MgCl, 7 mM phosphate buffer pH 6.0, 20% glycerol). The centrifugation and resuspension of the cells is repeated as described above. Four hundred µl of the resuspended cells are added to the cuvette of a Genepulser with a 0.4 cm electrode gap. Plasmid DNA is added to the cells in the cuvette and maintained at 4° C. for 10 minutes. The plasmid DNA is transferred into the cells by electroporation using a capacitance of 25 µF and a field strength of 1300 V. The treated cells were then maintained at 4° C. for an additional 10 minutes, then diluted with 1.6 ml L-broth and incubated for 4 hours at 30° C. on a rotary shaker at 250 rpm. The cells were then plated on T3 agar (3 g Tryptone, 2 g Tryptose, 1.5 g Yeast Extract, 0.05 g $MgCl_2$, 50 mM sodium phosphate pH 6.8) containing 25 µg/ml erythromycin and incubated at 30° C. for 24–36 hours to visualize colonies. Single colonies were picked from the plates and streaked out on fresh T3 containing erythromycin and grown to sporulation. Transformed cells of CGB315 which produced crystalline protein bodies, indicative of expression of the novel toxin genes, were identified microscopically.

The recombinant strain of *Bacillus thuringiensis* containing pCIB5618 and expressing the novel toxin gene isolated from clone CGB316#A was designated CGB311. CGB311 was deposited on Jun. 1, 1994 with the Agricultural Research Service, Patent Culture Collection (NRRL), Northern Regional Research Center, 1815 North University Street, Peoria, Ill. 61604, U.S.A. and was assigned accession number NRRL B-21273.

Example 4: Insect Bioassay of Novel Toxin Genes Expressed in Recombinant *Bacillus thuringiensis*

Insect bioassays were conducted by adding spore/crystal mixtures to artificial diet preparations. For example, molten Black Cutworm artificial insect diet was poured into 45 mm Gellman snap-cap Petri dishes. Test solutions of spore/crystals mixtures from the recombinant *Bacillus thuringiensis strain CGB*311 were made using dilutions of a 1 mg/ml suspension in 0.01% Triton X-100 designed to provide a range of test concentrations for each sample. After solidification of the molten diet, 100 µl of the appropriate dilution of Bt in 0.01% Triton X-100 was spread over the surface and the plates are air dried. Ten insects at the first instar of *Spodoptera exguia* (beet armyworm), *S. fugiperda* (fall armyworm), or *Ostrinia nubilalis* (European corn borer) and which were less than 24 hours old were placed onto the diet surface for a total of 30 insects at the first instar for each concentration of spore/crystal tested. The assay was incubated at 30° C. in complete darkness for 72 hours. The percent mortality was recorded at the end of the assay period.

The assay for Heliothis virescens(tobacco budworm) was similar to the above assay with the following differences. Costar 24-well cell culture clusters were used with a single well surface area of 2.26 $cm^2$ and 15 µl of the spore/crystal dilution was applied to the surface of the solidified artificial diet. One *H. virescens* larvae which is less than 24 hours old is placed in each well for a total of 24 insects for each concentration of spore/crystal tested. The wells were covered with two pieces of Parafilm and a piece of Teri-Kimwipe® to prevent escape of the insects from the wells. The assay was incubated at 30° C. for 72 hours after which percent mortality was recorded. Background mortality for all assays was 0–15%.

The results of the bioassay of the novel toxins are summarized in Table 2.

TABLE 2

| Relative Activities of Novel Toxins on Selected Insects | | | | |
|---|---|---|---|---|
| Insect Toxins | *Spodoptera exigua* | *Spodoptera fugiperda* | *Heliothis virescens* | *Ostrinia nubilalis* |
| CGB311 containing cryIE(c) of the present invention | − | − | ++ | − |
| CryIE(a) | ++ | na | − | na |

++ = 10 $ng/cm^2$ ≤ $LC_{50}$ ≤ 100 $ng/cm^2$
+ = 100 $ng/cm^2$ ≤ $LC_{50}$ ≤ 1000 $ng/cm^2$
− = $LC_{50}$ ≥ 1000 $ng/cm^2$
na = data not available

Example 5: SDS-PAGE Analysis of the Novel Toxin Protein

Spore/crystal stocks of the recombinant strain CGB311 were prepared (20 mg/ml) in 0.1% Triton X-100 from lyophilized powders. A 100 µl portion of the stock was treated with 25 µl of 0.4N NaOH for 5 min at room temperature, then 125 µl of 4% SDS, 20% glycerol, 10% β-mercapto-ethanol, 0.01% bromophenol blue, and 0.125M Tris-HCL pH 6.8 (Brussock, S. M., and T. C. Currier (1990) Analytical chemistry of *B. thuringiensis*. L. A. Hickle and W. L. Fitch, editors, American Chemical Society). This solution was then heated at 100° C. for 2 min. Samples were centrifuged for 60 s at 14,000 g in an Eppendorf 5415 microfuge. The samples were loaded on a 10% SDS-PAGE (Novex) and run as described by the supplier. Gels were stained in 0.2% Coomassie blue, 40% methanol and 10% acetic acid for 30 min at room temperature and destained with 40% methanol, 10% acetic acid. Gels were scanned using Molecular Dynamics Personal Densitometer and data was analyzed using Microsoft Excel. FIG. 1 shows a protein band at the expected molecular weight based on the deduced protein sequence.

Example 6: Transformation of Maize with the Novel Toxin Gene

Transformation of maize with the novel toxin gene prepared according to any of the above methods is achieved by microprojectile bombardment of either immature zygotic embryos or serially-propagatable Type I embryogenic callus.

For transformation using immature zygotic embryos, ears are self-pollinated and immature zygotic embryos are obtained approximately 10 days later. Approximately eight hundred immature zygotic embryos are divided among different target plates containing a medium capable of inducing and supporting the formation of embryogenic callus. The immature zygotic embryos are transferred immediately to the same medium but containing 12% sucrose. After 5 hours, the immature zygotic embryos are bombarded with a plasmid or plasmids using the PDS-1000/He device from BioRad. The plasmid or plasmids comprise a selectable marker such as a gene conferring resistance to phosphinothricin and the novel toxin gene prepared for delivery to and expression in maize according to the above description. The plasmid or plasmids are precipitated onto 1 μm gold particles essentially according to the published procedure from BioRad. The particles are delivered using a burst pressure of 1550 psi of helium. Each target plate is shot twice with the plasmid and gold particle preparation. Since the plasmid or plasmids comprise a chimetic gene coding for resistance to phosphinothricin this substance is used to select transformed cells in vitro. The selection agent is applied at 10 mg/L on the day of gene delivery and increased to 40 mg/L after approximately one month. The embryogenic callus so obtained is regenerated in the presence of the selection agent phosphinothricin. Plants are obtained from the phosphinothricin resistant embryogenic callus lines. The regenerated plants are assayed for resistance to a susceptible insect. All the plants that are resistant to the insect also express the introduced chimeric novel toxin gene as evidenced by the detection of novel toxin protein in the plant using an ELISA assay. Plants resistant to the insect and expressing the introduced novel toxin gene are transformed.

For transformation of maize using Type I embryogenic callus, the callus is obtained from immature zygotic embryos using standard culture techniques. For gene delivery, approximately 300 mg of the Type I callus is prepared by either chopping with a scalpel blade or by subculturing 3–5 days prior to gene delivery. Prior to gene delivery, the prepared callus is placed onto semi-solid culture medium again containing 12% sucrose. After approximately 4 hours, the tissue is bombarded using the PDS-1000/He Biolistic device from BioRad. The plasmid or plasmids comprising a selectable marker such as a gene conferring resistance to phosphinothricin and the novel toxin gene prepared for delivery to and expression in maize according to the above description are precipitated onto 1 μm gold particles using essentially the standard protocol from BioRad. Approximately 16 hours after gene delivery the callus is transferred to standard culture medium containing 2% sucrose and 1 mg/L phosphinothricin. The callus is subcultured on selection for 8 weeks, after which surviving and growing callus is transferred to standard regeneration medium for the production of plants. The regenerated plants are assayed for resistance to a susceptible insect. All the plants that are resistant to the insect also express the introduced chimetic novel toxin gene as evidenced by the detection of novel toxin protein in the plant using an ELISA assay. Plants resistant to the insect and expressing the introduced novel toxin gene are transformed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated DNA molecule encoding a toxin protein wherein said toxin protein comprises a sequence selected from the group consisting of Sub-Sequence A (SEQ ID NO:3) and Sub-Sequence B (SEQ ID NO:4) and is active against *Heliothis* species.

2. The isolated DNA molecule of claim 1 wherein said toxin protein comprises both Sub-Sequence A (SEQ ID NO:3) and Sub-Sequence B (SEQ ID NO:4).

3. The isolated DNA molecule of claim 1 wherein said toxin protein is a recombinant protein.

4. The isolated DNA molecule of claim 1, wherein said toxin protein is CryIE(c) having the amino acid sequence set forth in SEQ ID NO:2.

5. The isolated DNA molecule of claim 4 having the nucleotide sequence set forth in SEQ ID NO:1.

6. The isolated DNA molecule of claim 1 which has been optimized for expression in maize.

7. The isolated DNA molecule of claim 6 which has been truncated to encode the toxic core fragment of the toxin protein CryIE(c).

8. A recombinant microorganism transformed with isolated DNA molecule of claim 1.

9. The recombinant microorganism of claim 8 wherein said recombinant microorganism is selected from the group consisting of members of the genus *Bacillus, Pseudomonas, Caulobacter, Agmellenum, Rhizobium,* and *Clavibacter.*

10. The recombinant microorganism of claim 8 wherein said recombinant microorganism is the nuclear polyhedrosis virus *Autographica californica.*

11. An entomocidal composition comprising the recombinant microorganism of claim 8.

12. The entomocidal composition of claim 11 wherein said recombinant microorganism is selected from the group consisting of the members of the genus *Bacillus, Pseudomonas, Caulobacter, Agmellenum, Rhizobium,* and *Clavibacter.*

13. The entomocidal composition of claim 11 wherein said recombinant microorganism is the nuclear polyhedrosis virus *Autographica californica.*

14. A transformed plant comprising a DNA molecule encoding a toxin protein wherein said toxin protein comprises a sequence selected from the group consisting of Sub-Sequence A (SEQ ID NO:3), Sub-Sequence B (SEQ ID NO:4) and a combination of Sub-Sequence A (SEQ ID NO:3) plus Sub-Sequence B (SEQ ID NO:4) wherein said toxin protein is active against *Heliothis* species.

15. A transformed plant comprising the DNA molecule of claim 6.

16. A transformed plant comprising the DNA molecule of claim 7.

17. The transformed plant of claim 14 wherein said plant is selected from the group consisting of maize, wheat, barley, rice, tobacco, cotton, and soybean.

18. The transformed plant of claim 15 wherein said plant is selected from the group consisting of maize, wheat, barley, rice, tobacco, cotton, and soybean.

19. The transformed plant of claim 16 wherein said plant is selected from the group consisting of maize, wheat, barley, rice, tobacco, cotton, and soybean.

20. An isolated protein molecule comprising a sequence selected from the group consisting of Sub-Sequence A (SEQ ID NO:3) and Sub-Sequence B (SEQ ID NO:4) which is active against *Heliothis* species.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 4003 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: kurstaki
( C ) INDIVIDUAL ISOLATE: CGB316

( i x ) FEATURE:
( A ) NAME/KEY: promoter
( B ) LOCATION: 96..124
( D ) OTHER INFORMATION: /function="putative promoter region"

( i x ) FEATURE:
( A ) NAME/KEY: RBS
( B ) LOCATION: 185..190

( i x ) FEATURE:
( A ) NAME/KEY: CDS (B) LOCATION: 196..3723
(D) OTHER INFORMATION: /product="Full-length CryIE(c) protein"

(ix) FEATURE:
(A) NAME/KEY: misc_feature
(B) LOCATION: 1191..1590
(D) OTHER INFORMATION: /note="This region of the CryIE(c) DNA sequence encodes the amino acid sequence designated Sub-Sequence A"

(ix) FEATURE:
(A) NAME/KEY: misc_feature
(B) LOCATION: 1591..2061
(D) OTHER INFORMATION: /note="This region of the CryIE(c) DNA sequence encodes the amino acid sequence designated Sub-Sequence B"

(xi) SEQUENCE DESCRIPTION: SEQ ID NO:1:

AAGTATGGGC GAGAAATAAG TGAATTATTA GCACCCTGGG TCTATTTTAG CCCCAGGGCA 60

TAAATTGATA TTTTTTAATA TTGGTTGCAC TTTGTGTATT TTTTCATAGA ATGATTCATA 120

TACTTTACAT TGTAATACGA TACGAGGTTT TTAGTTTTAA AGAACAACTA TTATGATGAA 180

AAACGGAGGG TTATA ATG GAT AAT AAT AAT CAA AAT CAA TGC ATA CCT TAC 231
Met Asp Asn Asn Asn Gln Asn Gln Cys Ile Pro Tyr
1 5 10

AAT TGT TTA AGT AAT CCT GAA TTA GAG ATA TTA GAG ATT GAA AGA TCA 279
Asn Cys Leu Ser Asn Pro Glu Leu Glu Ile Leu Glu Ile Glu Arg Ser
15 20 25

AAT AAT ACC GTA GTA GAA GAC ATC ACC TTG GGG CTG AGT CGT CTG CTC 327
Asn Asn Thr Val Val Glu Asp Ile Thr Leu Gly Leu Ser Arg Leu Leu
30 35 40

GTT TCC GCA ATT CCA CTA GGG GAT TTT ATA CTT GGC TTG TTT GAT GTA 375
Val Ser Ala Ile Pro Leu Gly Asp Phe Ile Leu Gly Leu Phe Asp Val
45 50 55 60

ATA TGG GGG GCT TTA GGT CGT TCA GAG TGG GAT ATA TTT TTA GAG CAA 423
Ile Trp Gly Ala Leu Gly Arg Ser Glu Trp Asp Ile Phe Leu Glu Gln
65 70 75

ATT GAG CTA TTG ATC GGC CAA AGA ATA GAG GAA TTT GCT AGG AAT CAG 471
Ile Glu Leu Leu Ile Gly Gln Arg Ile Glu Glu Phe Ala Arg Asn Gln
80 85 90

GCA ATT TCT AGA TTA GAA GGG CTA AGC AAT CTT TAT CGA ATT TAC ACA 519
Ala Ile Ser Arg Leu Glu Gly Leu Ser Asn Leu Tyr Arg Ile Tyr Thr
95 100 105

AAT GCT TTT AAA GAC TGG GAA GCA GAT CCT ACT AAT CTA GAA TTA AAA 567
Asn Ala Phe Lys Asp Trp Glu Ala Asp Pro Thr Asn Leu Glu Leu Lys
110 115 120

GAA GAG ATG CGT ACT CAA TTT AAT GAC ATG AAC AGT GCT TTT ACA ACA 615
Glu Glu Met Arg Thr Gln Phe Asn Asp Met Asn Ser Ala Phe Thr Thr
125 130 135 140

GCT ATT CCT CTT TTT TCA GTT CGA GGT TAT GAA CTT CCT CTT TTA TCA 663
Ala Ile Pro Leu Phe Ser Val Arg Gly Tyr Glu Leu Pro Leu Leu Ser
145 150 155

GTA TAT GTT CAA GCT GCA AAT TTA CAT TTA TCA GTT TTA AGA GAT GTT 711
Val Tyr Val Gln Ala Ala Asn Leu His Leu Ser Val Leu Arg Asp Val
160 165 170

TCA GTG TTT GGA CAA CGT TGG GGA TTT GAC GTA GCA ACA GTC AAT CGT 759
Ser Val Phe Gly Gln Arg Trp Gly Phe Asp Val Ala Thr Val Asn Arg
175 180 185

CGT TAT GAT GAT TTA ACT ACG AAT ATA GGC GAC TAC ACA GAT TAT GCT 807
Arg Tyr Asp Asp Leu Thr Thr Asn Ile Gly Asp Tyr Thr Asp Tyr Ala
190 195 200

TTA AGC TGG TAT AAT ACG GGA TTA AAC CGT TTA CCA CGT AAT GAT GGG 855
Leu Ser Trp Tyr Asn Thr Gly Leu Asn Arg Leu Pro Arg Asn Asp Gly

| | | | | | | | | | | | | | | | | |
|---|---|---|---|---|---|---|---|---|---|---|---|---|---|---|---|---|
| 205 | | | | | 210 | | | | | 215 | | | | | 220 | |
| CTG | CGA | GGA | TGG | GCA | AGA | TTT | AAT | AGG | TTT | AGA | AGA | GAG | TTA | ACA | ATA | 903 |
| Leu | Arg | Gly | Trp | Ala 225 | Arg | Phe | Asn | Arg 230 | Phe | Arg | Arg | Glu | Leu | Thr 235 | Ile | |
| TCA | GTA | TTA | GAT | ATT | ATT | TCT | TTT | TTC | CAA | AAT | TAC | GAT | TCT | AGA | TTA | 951 |
| Ser | Val | Leu | Asp 240 | Ile | Ile | Ser | Phe | Phe 245 | Gln | Asn | Tyr | Asp | Ser 250 | Arg | Leu | |
| TAT | CCA | ATT | CCA | ACA | ATC | TCC | CAA | TTA | ACG | CGG | GAA | GTA | TAT | ACA | GAT | 999 |
| Tyr | Pro | Ile 255 | Pro | Thr | Ile | Ser | Gln 260 | Leu | Thr | Arg | Glu | Val 265 | Tyr | Thr | Asp | |
| CCG | GTA | ATT | AAT | ATA | ACT | GAT | TAT | AGA | GTT | ACC | CCA | AGT | TTC | GAG | AGT | 1047 |
| Pro | Val | Ile 270 | Asn | Ile | Thr | Asp 275 | Tyr | Arg | Val | Thr | Pro 280 | Ser | Phe | Glu | Ser | |
| ATT | GAA | AAC | TCA | GCC | ATT | AGA | AGC | CCC | CAT | CTT | ATG | GAT | TTC | TTA | ACT | 1095 |
| Ile 285 | Glu | Asn | Ser | Ala | Ile 290 | Arg | Ser | Pro | His | Leu 295 | Met | Asp | Phe | Leu | Thr 300 | |
| AAT | ATA | ATT | ATT | GAC | ACT | GAT | TTA | ATA | AGA | GGT | GTT | TAC | TAT | TGG | GCA | 1143 |
| Asn | Ile | Ile | Ile | Asp 305 | Thr | Asp | Leu | Ile | Arg 310 | Gly | Val | Tyr | Tyr | Trp 315 | Ala | |
| GGA | CAT | CGT | ATA | AAT | TCT | CGC | TTT | ACC | GGG | ACC | GCT | TTT | CCA | CAT | ATA | 1191 |
| Gly | His | Arg | Ile 320 | Asn | Ser | Arg | Phe | Thr 325 | Gly | Thr | Ala | Phe | Pro 330 | His | Ile | |
| ATA | ACA | TCT | CCT | CAA | TAT | GGA | ATA | ACT | GCA | AAC | GCA | GAA | CCA | AGA | CGT | 1239 |
| Ile | Thr | Ser 335 | Pro | Gln | Tyr | Gly | Ile 340 | Thr | Ala | Asn | Ala | Glu 345 | Pro | Arg | Arg | |
| ACA | ATA | GCG | CCT | GGT | CCT | TTT | CAA | GGT | GTG | CCT | TCC | CTA | CTT | TAT | AGA | 1287 |
| Thr | Ile | Ala 350 | Pro | Gly | Pro | Phe | Gln 355 | Gly | Val | Pro | Ser | Leu 360 | Leu | Tyr | Arg | |
| ACA | CTA | TCA | GAC | CCT | TTC | TTC | CGA | AGA | TCA | GAC | AAT | ATT | AGT | CCA | ACC | 1335 |
| Thr | Leu | Ser | Asp | Pro 370 | Phe | Phe | Arg | Arg | Ser 375 | Asp | Asn | Ile | Ser | Pro 380 | Thr | |
| Thr 365 | | | | | | | | | | | | | | | | |
| TTA | GGG | ATA | AAT | GTA | GTA | CAG | GGG | GTA | GGG | TTC | TTA | CAA | CCA | AAT | AAT | 1383 |
| Leu | Gly | Ile | Asn | Val 385 | Val | Gln | Gly | Val 390 | Gly | Phe | Leu | Gln | Pro 395 | Asn | Asn | |
| TTT | GAA | TCT | CTA | TAT | AGA | AGG | AGA | GGG | ACA | GTA | GAT | TCT | CTC | GAT | GAG | 1431 |
| Phe | Glu | Ser | Leu 400 | Tyr | Arg | Arg | Arg | Gly 405 | Thr | Val | Asp | Ser | Leu 410 | Asp | Glu | |
| TTG | CCA | ATT | GAT | GGT | GAA | AAT | CCA | TTA | GTT | GGA | TAT | AGT | CAT | CGA | TTA | 1479 |
| Leu | Pro | Ile 415 | Asp | Gly | Glu | Asn | Pro 420 | Leu | Val | Gly | Tyr | Ser 425 | His | Arg | Leu | |
| AGT | CAC | GTT | ACA | TTA | ACC | AGG | TCA | TTA | TTT | AAT | ACT | AAT | ATA | ACT | AGC | 1527 |
| Ser | His | Val 430 | Thr | Leu | Thr | Arg | Ser 435 | Leu | Phe | Asn | Thr | Asn 440 | Ile | Thr | Ser | |
| CTG | CCA | ACA | TTT | GTT | TGG | ACA | CAT | CAC | AGT | GCT | ACT | GAT | ACA | AAT | ACA | 1575 |
| Leu | Pro | Thr | Phe | Val 450 | Trp | Thr | His | His | Ser 455 | Ala | Thr | Asp | Thr | Asn 460 | Thr | |
| Leu 445 | | | | | | | | | | | | | | | | |
| ATT | GCT | CCA | GAT | GTC | ATT | ACC | CAA | ATA | CCG | TTA | GTA | AAG | GCT | TTC | AAT | 1623 |
| Ile | Ala | Pro | Asp | Val 465 | Ile | Thr | Gln | Ile | Pro 470 | Leu | Val | Lys | Ala | Phe 475 | Asn | |
| CTT | CAT | TCA | GGT | GCC | ACG | GTT | GCT | AGA | GGG | CCA | GGA | TTT | ACA | GGT | GGG | 1671 |
| Leu | His | Ser | Gly | Ala 480 | Thr | Val | Ala | Arg | Gly 485 | Pro | Gly | Phe | Thr | Gly 490 | Gly | |
| GAT | ATC | CTT | CGA | AGA | ACG | AAT | GTT | GGT | AAC | TTT | GGA | GAT | ATG | CGT | GTA | 1719 |
| Asp | Ile | Leu | Arg 495 | Arg | Thr | Asn | Val | Gly 500 | Asn | Phe | Gly | Asp | Met 505 | Arg | Val | |
| AAT | ATT | ACT | GCA | CCA | CTA | TCA | CAA | AGA | TAT | CGA | GTA | AGG | ATT | CGT | TAT | 1767 |
| Asn | Ile | Thr 510 | Ala | Pro | Leu | Ser | Gln 515 | Arg | Tyr | Arg | Val | Arg 520 | Ile | Arg | Tyr | |
| GCT | TCT | ACT | ACA | AAT | TTA | CGA | TTC | CAT | ACA | TCA | ATT | AAC | GGA | AGA | GCT | 1815 |
| Ala | Ser | Thr | Thr | Asn | Leu | Arg | Phe | His | Thr | Ser | Ile | Asn | Gly | Arg | Ala | |

| | | | | | | | | | | | | | | | | |
|---|---|---|---|---|---|---|---|---|---|---|---|---|---|---|---|---|
| 525 | | | | | 530 | | | | | 535 | | | | | 540 | |
| ATT | AAT | CAG | GCG | GAT | TTT | CCA | GCT | ACT | ATG | AAT | AGT | GGG | GGT | AAT | TTA | 1863 |
| Ile | Asn | Gln | Ala | Asp | Phe | Pro | Ala | Thr | Met | Asn | Ser | Gly | Gly | Asn | Leu | |
| | | | 545 | | | | | 550 | | | | | 555 | | | |
| CAG | TCC | GGA | AGC | TTC | AGG | ATT | GCA | GGT | TTT | ACT | ACT | CCA | TTT | ACC | TTT | 1911 |
| Gln | Ser | Gly | Ser | Phe | Arg | Ile | Ala | Gly | Phe | Thr | Thr | Pro | Phe | Thr | Phe | |
| | | | 560 | | | | | 565 | | | | | 570 | | | |
| TCA | GAT | GCA | CTA | AGC | ACA | TTC | ACA | ATA | GGT | GCT | TTT | GGC | TTC | TCT | TCA | 1959 |
| Ser | Asp | Ala | Leu | Ser | Thr | Phe | Thr | Ile | Gly | Ala | Phe | Gly | Phe | Ser | Ser | |
| | | | 575 | | | | | 580 | | | | | 585 | | | |
| GGT | AAC | GAA | GTT | TAT | ATA | GAT | CGA | ATT | GAA | TTT | GTT | CCG | GCA | GAA | GTA | 2007 |
| Gly | Asn | Glu | Val | Tyr | Ile | Asp | Arg | Ile | Glu | Phe | Val | Pro | Ala | Glu | Val | |
| | | | 590 | | | | | 595 | | | | | 600 | | | |
| ACC | TTT | GAG | GCA | GAA | TAT | GAT | CTA | GAA | AGA | GCA | CAA | AAG | GCG | GTG | AAT | 2055 |
| Thr | Phe | Glu | Ala | Glu | Tyr | Asp | Leu | Glu | Arg | Ala | Gln | Lys | Ala | Val | Asn | |
| 605 | | | | | 610 | | | | | 615 | | | | | 620 | |
| GCG | CTG | TTT | ACT | TCT | TCT | AAT | CAA | ATC | GGG | TTA | AAA | ACA | GAT | GTA | ACG | 2103 |
| Ala | Leu | Phe | Thr | Ser | Ser | Asn | Gln | Ile | Gly | Leu | Lys | Thr | Asp | Val | Thr | |
| | | | | 625 | | | | | 630 | | | | | 635 | | |
| GAT | TAT | CAT | ATT | GAT | CAA | GTA | TCC | AAT | CTA | GTT | GAA | TGC | TTA | TCG | GAT | 2151 |
| Asp | Tyr | His | Ile | Asp | Gln | Val | Ser | Asn | Leu | Val | Glu | Cys | Leu | Ser | Asp | |
| | | | 640 | | | | | 645 | | | | | 650 | | | |
| GAA | TTT | TGT | CTG | GAT | GAA | AAG | CGA | GAA | TTG | TCC | GAG | AAA | GTC | AAA | CAT | 2199 |
| Glu | Phe | Cys | Leu | Asp | Glu | Lys | Arg | Glu | Leu | Ser | Glu | Lys | Val | Lys | His | |
| | | 655 | | | | | 660 | | | | | 665 | | | | |
| GCG | AAG | CGA | CTC | AGT | GAT | GAG | CGG | AAT | TTA | CTT | CAA | GAT | CCA | AAC | TTT | 2247 |
| Ala | Lys | Arg | Leu | Ser | Asp | Glu | Arg | Asn | Leu | Leu | Gln | Asp | Pro | Asn | Phe | |
| | 670 | | | | | 675 | | | | | 680 | | | | | |
| AGA | GGG | ATC | AAT | AGA | CAA | CTA | GAC | CGT | GGC | TGG | AGA | GGA | AGT | ACG | GAT | 2295 |
| Arg | Gly | Ile | Asn | Arg | Gln | Leu | Asp | Arg | Gly | Trp | Arg | Gly | Ser | Thr | Asp | |
| 685 | | | | | 690 | | | | | 695 | | | | | 700 | |
| ATT | ACC | ATC | CAA | GGA | GGA | GAT | GAC | GTA | TTC | AAA | GAG | AAT | TAC | GTC | ACA | 2343 |
| Ile | Thr | Ile | Gln | Gly | Gly | Asp | Asp | Val | Phe | Lys | Glu | Asn | Tyr | Val | Thr | |
| | | | | 705 | | | | | 710 | | | | | 715 | | |
| CTA | CCG | GGT | ACC | TTT | GAT | GAG | TGC | TAT | CCA | ACG | TAT | TTA | TAT | CAA | AAA | 2391 |
| Leu | Pro | Gly | Thr | Phe | Asp | Glu | Cys | Tyr | Pro | Thr | Tyr | Leu | Tyr | Gln | Lys | |
| | | | 720 | | | | | 725 | | | | | 730 | | | |
| ATA | GAT | GAG | TCA | AAA | TTA | AAA | GCC | TAT | ACC | CGT | TAT | CAA | TTA | AGA | GGG | 2439 |
| Ile | Asp | Glu | Ser | Lys | Leu | Lys | Ala | Tyr | Thr | Arg | Tyr | Gln | Leu | Arg | Gly | |
| | | 735 | | | | | 740 | | | | | 745 | | | | |
| TAT | ATC | GAG | GAT | AGT | CAA | GAC | TTA | GAA | ATC | TAT | TTA | ATT | CGC | TAC | AAT | 2487 |
| Tyr | Ile | Glu | Asp | Ser | Gln | Asp | Leu | Glu | Ile | Tyr | Leu | Ile | Arg | Tyr | Asn | |
| | 750 | | | | | 755 | | | | | 760 | | | | | |
| GCA | AAA | CAT | GAA | ACA | GTA | AAT | GTG | CCA | GGT | ACG | GGT | TCT | TTA | TGG | CCG | 2535 |
| Ala | Lys | His | Glu | Thr | Val | Asn | Val | Pro | Gly | Thr | Gly | Ser | Leu | Trp | Pro | |
| 765 | | | | | 770 | | | | | 775 | | | | | 780 | |
| CTT | TCA | GTC | GAA | AGT | CCA | ATC | GGA | AAG | TGT | GGA | GAA | CTA | AAT | CGA | TGC | 2583 |
| Leu | Ser | Val | Glu | Ser | Pro | Ile | Gly | Lys | Cys | Gly | Glu | Leu | Asn | Arg | Cys | |
| | | | | 785 | | | | | 790 | | | | | 795 | | |
| GCG | CCA | CAC | CTT | GAA | TGG | AAT | CCT | GAT | CTA | GAT | TGT | TCC | TGC | AGA | GAC | 2631 |
| Ala | Pro | His | Leu | Glu | Trp | Asn | Pro | Asp | Leu | Asp | Cys | Ser | Cys | Arg | Asp | |
| | | | 800 | | | | | 805 | | | | | 810 | | | |
| GGG | GAA | AAA | TGT | GCC | CAT | CAT | TCT | CAT | CAT | TTC | TCC | TTG | GAC | ATT | GAT | 2679 |
| Gly | Glu | Lys | Cys | Ala | His | His | Ser | His | His | Phe | Ser | Leu | Asp | Ile | Asp | |
| | | 815 | | | | | 820 | | | | | 825 | | | | |
| GTT | GGA | TGT | ACA | GAC | TTA | AAT | GAG | GAC | TTA | GGT | GTA | TGG | GTG | ATA | TTC | 2727 |
| Val | Gly | Cys | Thr | Asp | Leu | Asn | Glu | Asp | Leu | Gly | Val | Trp | Val | Ile | Phe | |
| | 830 | | | | | 835 | | | | | 840 | | | | | |
| AAG | ATT | AAG | ACG | CAA | GAT | GGC | CAT | GCA | AGA | TTA | GGA | AAT | CTA | GAA | TTT | 2775 |
| Lys | Ile | Lys | Thr | Gln | Asp | Gly | His | Ala | Arg | Leu | Gly | Asn | Leu | Glu | Phe | |

```
845                          850                          855                          860

CTC GAA GAG AAA CCA TTA GTA GGA GAA GCA CTA GCT CGT GTG AAA AGA       2823
Leu Glu Glu Lys Pro Leu Val Gly Glu Ala Leu Ala Arg Val Lys Arg
            865                 870                 875

GCG GAG AAA AAA TGG AGA GAC AAA CGT GAA AAA TTG GAA TTG GAA ACA       2871
Ala Glu Lys Lys Trp Arg Asp Lys Arg Glu Lys Leu Glu Leu Glu Thr
            880                 885                 890

AAT ATT GTT TAT AAA GAG GCA AAA GAA TCT GTA GAT GCT TTA TTT GTA       2919
Asn Ile Val Tyr Lys Glu Ala Lys Glu Ser Val Asp Ala Leu Phe Val
            895                 900                 905

AAC TCT CAA TAT GAT AGA TTA CAA GCG GAT ACC AAC ATC GCG ATG ATT       2967
Asn Ser Gln Tyr Asp Arg Leu Gln Ala Asp Thr Asn Ile Ala Met Ile
910                 915                 920

CAT GCG GCA GAT AAA CGC GTT CAT AGC ATT CGA GAA GCT TAT CTG CCT       3015
His Ala Ala Asp Lys Arg Val His Ser Ile Arg Glu Ala Tyr Leu Pro
925                 930                 935                 940

GAG CTG TCT GTG ATT CCG GGT GTC AAT GCG GCT ATT TTT GAA GAA TTA       3063
Glu Leu Ser Val Ile Pro Gly Val Asn Ala Ala Ile Phe Glu Glu Leu
            945                 950                 955

GAA GGG CGT ATT TTC ACT GCA TTC TCC CTA TAT GAT GCG AGA AAT GTC       3111
Glu Gly Arg Ile Phe Thr Ala Phe Ser Leu Tyr Asp Ala Arg Asn Val
        960                 965                 970

ATT AAA AAT GGT GAT TTT AAT TAT GGC TTA TCC TGC TGG AAC GTG AAA       3159
Ile Lys Asn Gly Asp Phe Asn Tyr Gly Leu Ser Cys Trp Asn Val Lys
        975                 980                 985

GGG CAT GTA GAT GTA GAA GAA CAA AAC AAC CAC CGT TCG GTC CTT GTT       3207
Gly His Val Asp Val Glu Glu Gln Asn Asn His Arg Ser Val Leu Val
990                 995                 1000

GTT CCG GAA TGG GAA GCA GAA GTG TCA CAA GAA GTT CGT GTC TGT CCG       3255
Val Pro Glu Trp Glu Ala Glu Val Ser Gln Glu Val Arg Val Cys Pro
1005                1010                1015                1020

GGT CGT GGC TAT ATC CTT CGT GTC ACA GCT TAC AAG GAG GGA TAT GGA       3303
Gly Arg Gly Tyr Ile Leu Arg Val Thr Ala Tyr Lys Glu Gly Tyr Gly
                1025                1030                1035

GAA GGT TGC GTA ACC ATT CAT GAG ATC GAG AAC AAT ACA GAC GAA CTG       3351
Glu Gly Cys Val Thr Ile His Glu Ile Glu Asn Asn Thr Asp Glu Leu
            1040                1045                1050

AAG TTT AGC AAC TGT GTA GAA GAG GAA GTA TAT CCA AAC AAC ACG GTA       3399
Lys Phe Ser Asn Cys Val Glu Glu Glu Val Tyr Pro Asn Asn Thr Val
        1055                1060                1065

ACG TGT AAT GAT TAT ACT GCG ACT CAA GAA GAA TAT GAG GGT ACG TAC       3447
Thr Cys Asn Asp Tyr Thr Ala Thr Gln Glu Glu Tyr Glu Gly Thr Tyr
        1070                1075                1080

ACT TCT CGT AAT CGA GGA TAT GAC GGA GCC TAT GAA AGC AAT TCT TCT       3495
Thr Ser Arg Asn Arg Gly Tyr Asp Gly Ala Tyr Glu Ser Asn Ser Ser
1085                1090                1095                1100

GTA CCA GCT GAT TAT GCA TCA GCC TAT GAA GAA AAA GCG TAT ACA GAT       3543
Val Pro Ala Asp Tyr Ala Ser Ala Tyr Glu Glu Lys Ala Tyr Thr Asp
                1105                1110                1115

GGA CGA AGA GAC AAT CCT TGT GAA TCT AAC AGA GGA TAT GGG GAT TAC       3591
Gly Arg Arg Asp Asn Pro Cys Glu Ser Asn Arg Gly Tyr Gly Asp Tyr
            1120                1125                1130

ACA CCA CTA CCA GCT GGC TAT GTG ACA AAA GAA TTA GAG TAC TTC CCA       3639
Thr Pro Leu Pro Ala Gly Tyr Val Thr Lys Glu Leu Glu Tyr Phe Pro
        1135                1140                1145

GAA ACC GAT AAG GTA TGG ATT GAG ATC GGA GAA ACG GAA GGA ACA TTT       3687
Glu Thr Asp Lys Val Trp Ile Glu Ile Gly Glu Thr Glu Gly Thr Phe
1150                1155                1160

ATC GTG GAC AGC GTG GAA TTA CTC CTT ATG GAG GAA TAGTCTCATG            3733
Ile Val Asp Ser Val Glu Leu Leu Leu Met Glu Glu
```

```
1165              1170              1175

CAAACACTGG  TTTAAATATC  GTTTTCAAAT  CAATTGTCCA  AGAGCAGCAT  TACAAATAGA    3793

TAAGTAATTT  GTTGTAATGA  AAAACGGACA  TCACCTCCAT  TGAAACGGAG  TAGTGTCCGT    3853

TTTACTATGT  TATTTTCTAG  TAATACATAT  GTATAGAGCA  ACTTAATCAA  GCAGAGATAT    3913

TTTCACCTAT  CGATGAAAAT  ATCTCTGCTT  TTTCTTTTTT  TTATTTGGTA  TATGCTTTAC    3973

TTGTAATCGA  AAATAAAGCA  CTAATAAGAG                                        4003
```

( 2 ) INFORMATION FOR SEQ ID NO:2:

( i ) SEQUENCE CHARACTERISTICS:
        ( A ) LENGTH: 1176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Asn  Asn  Asn  Gln  Asn  Gln  Cys  Ile  Pro  Tyr  Asn  Cys  Leu  Ser
 1              5                        10                       15

Asn  Pro  Glu  Leu  Glu  Ile  Leu  Glu  Ile  Glu  Arg  Ser  Asn  Asn  Thr  Val
              20                        25                       30

Val  Glu  Asp  Ile  Thr  Leu  Gly  Leu  Ser  Arg  Leu  Leu  Val  Ser  Ala  Ile
         35                        40                       45

Pro  Leu  Gly  Asp  Phe  Ile  Leu  Gly  Leu  Phe  Asp  Val  Ile  Trp  Gly  Ala
     50                        55                       60

Leu  Gly  Arg  Ser  Glu  Trp  Asp  Ile  Phe  Leu  Glu  Gln  Ile  Glu  Leu  Leu
 65                       70                       75                       80

Ile  Gly  Gln  Arg  Ile  Glu  Glu  Phe  Ala  Arg  Asn  Gln  Ala  Ile  Ser  Arg
                   85                       90                       95

Leu  Glu  Gly  Leu  Ser  Asn  Leu  Tyr  Arg  Ile  Tyr  Thr  Asn  Ala  Phe  Lys
              100                       105                       110

Asp  Trp  Glu  Ala  Asp  Pro  Thr  Asn  Leu  Glu  Leu  Lys  Glu  Glu  Met  Arg
         115                       120                       125

Thr  Gln  Phe  Asn  Asp  Met  Asn  Ser  Ala  Phe  Thr  Thr  Ala  Ile  Pro  Leu
     130                       135                       140

Phe  Ser  Val  Arg  Gly  Tyr  Glu  Leu  Pro  Leu  Leu  Ser  Val  Tyr  Val  Gln
145                       150                       155                       160

Ala  Ala  Asn  Leu  His  Leu  Ser  Val  Leu  Arg  Asp  Val  Ser  Val  Phe  Gly
                   165                       170                       175

Gln  Arg  Trp  Gly  Phe  Asp  Val  Ala  Thr  Val  Asn  Arg  Arg  Tyr  Asp  Asp
              180                       185                       190

Leu  Thr  Thr  Asn  Ile  Gly  Asp  Tyr  Thr  Asp  Tyr  Ala  Leu  Ser  Trp  Tyr
         195                       200                       205

Asn  Thr  Gly  Leu  Asn  Arg  Leu  Pro  Arg  Asn  Asp  Gly  Leu  Arg  Gly  Trp
     210                       215                       220

Ala  Arg  Phe  Asn  Arg  Phe  Arg  Arg  Glu  Leu  Thr  Ile  Ser  Val  Leu  Asp
225                       230                       235                       240

Ile  Ile  Ser  Phe  Phe  Gln  Asn  Tyr  Asp  Ser  Arg  Leu  Tyr  Pro  Ile  Pro
                   245                       250                       255

Thr  Ile  Ser  Gln  Leu  Thr  Arg  Glu  Val  Tyr  Thr  Asp  Pro  Val  Ile  Asn
              260                       265                       270

Ile  Thr  Asp  Tyr  Arg  Val  Thr  Pro  Ser  Phe  Glu  Ser  Ile  Glu  Asn  Ser
         275                       280                       285

Ala  Ile  Arg  Ser  Pro  His  Leu  Met  Asp  Phe  Leu  Thr  Asn  Ile  Ile  Ile
     290                       295                       300
```

```
Asp Thr Asp Leu Ile Arg Gly Val Tyr Tyr Trp Ala Gly His Arg Ile
305                 310                 315                 320
Asn Ser Arg Phe Thr Gly Thr Ala Phe Pro His Ile Ile Thr Ser Pro
            325                 330                 335
Gln Tyr Gly Ile Thr Ala Asn Ala Glu Pro Arg Arg Thr Ile Ala Pro
            340                 345                 350
Gly Pro Phe Gln Gly Val Pro Ser Leu Leu Tyr Arg Thr Leu Ser Asp
            355                 360                 365
Pro Phe Arg Arg Ser Asp Asn Ile Ser Pro Thr Leu Gly Ile Asn
    370                 375                 380
Val Val Gln Gly Val Gly Phe Leu Gln Pro Asn Asn Phe Glu Ser Leu
385                 390                 395                 400
Tyr Arg Arg Arg Gly Thr Val Asp Ser Leu Asp Glu Leu Pro Ile Asp
                405                 410                 415
Gly Glu Asn Pro Leu Val Gly Tyr Ser His Arg Leu Ser His Val Thr
            420                 425                 430
Leu Thr Arg Ser Leu Phe Asn Thr Asn Ile Thr Ser Leu Pro Thr Phe
            435                 440                 445
Val Trp Thr His His Ser Ala Thr Asp Thr Asn Thr Ile Ala Pro Asp
    450                 455                 460
Val Ile Thr Gln Ile Pro Leu Val Lys Ala Phe Asn Leu His Ser Gly
465                 470                 475                 480
Ala Thr Val Ala Arg Gly Pro Gly Phe Thr Gly Gly Asp Ile Leu Arg
                485                 490                 495
Arg Thr Asn Val Gly Asn Phe Gly Asp Met Arg Val Asn Ile Thr Ala
            500                 505                 510
Pro Leu Ser Gln Arg Tyr Arg Val Arg Ile Arg Tyr Ala Ser Thr Thr
            515                 520                 525
Asn Leu Arg Phe His Thr Ser Ile Asn Gly Arg Ala Ile Asn Gln Ala
    530                 535                 540
Asp Phe Pro Ala Thr Met Asn Ser Gly Gly Asn Leu Gln Ser Gly Ser
545                 550                 555                 560
Phe Arg Ile Ala Gly Phe Thr Thr Pro Phe Thr Phe Ser Asp Ala Leu
                565                 570                 575
Ser Thr Phe Thr Ile Gly Ala Phe Gly Phe Ser Ser Gly Asn Glu Val
            580                 585                 590
Tyr Ile Asp Arg Ile Glu Phe Val Pro Ala Glu Val Thr Phe Glu Ala
            595                 600                 605
Glu Tyr Asp Leu Glu Arg Ala Gln Lys Ala Val Asn Ala Leu Phe Thr
    610                 615                 620
Ser Ser Asn Gln Ile Gly Leu Lys Thr Asp Val Thr Asp Tyr His Ile
625                 630                 635                 640
Asp Gln Val Ser Asn Leu Val Glu Cys Leu Ser Asp Glu Phe Cys Leu
                645                 650                 655
Asp Glu Lys Arg Glu Leu Ser Glu Lys Val Lys His Ala Lys Arg Leu
            660                 665                 670
Ser Asp Glu Arg Asn Leu Leu Gln Asp Pro Asn Phe Arg Gly Ile Asn
    675                 680                 685
Arg Gln Leu Asp Arg Gly Trp Arg Gly Ser Thr Asp Ile Thr Ile Gln
    690                 695                 700
Gly Gly Asp Asp Val Phe Lys Glu Asn Tyr Val Thr Leu Pro Gly Thr
705                 710                 715                 720
Phe Asp Glu Cys Tyr Pro Thr Tyr Leu Tyr Gln Lys Ile Asp Glu Ser
```

-continued

```
                            725                              730                             735
Lys  Leu  Lys  Ala  Tyr  Thr  Arg  Tyr  Gln  Leu  Arg  Gly  Tyr  Ile  Glu  Asp
               740                           745                      750

Ser  Gln  Asp  Leu  Glu  Ile  Tyr  Leu  Ile  Arg  Tyr  Asn  Ala  Lys  His  Glu
          755                      760                     765

Thr  Val  Asn  Val  Pro  Gly  Thr  Gly  Ser  Leu  Trp  Pro  Leu  Ser  Val  Glu
     770                     775                     780

Ser  Pro  Ile  Gly  Lys  Cys  Gly  Glu  Leu  Asn  Arg  Cys  Ala  Pro  His  Leu
785                 790                     795                               800

Glu  Trp  Asn  Pro  Asp  Leu  Asp  Cys  Ser  Cys  Arg  Asp  Gly  Glu  Lys  Cys
               805                      810                          815

Ala  His  His  Ser  His  His  Phe  Ser  Leu  Asp  Ile  Asp  Val  Gly  Cys  Thr
               820                      825                          830

Asp  Leu  Asn  Glu  Asp  Leu  Gly  Val  Trp  Val  Ile  Phe  Lys  Ile  Lys  Thr
          835                      840                     845

Gln  Asp  Gly  His  Ala  Arg  Leu  Gly  Asn  Leu  Glu  Phe  Leu  Glu  Glu  Lys
          850                      855                     860

Pro  Leu  Val  Gly  Glu  Ala  Leu  Ala  Arg  Val  Lys  Arg  Ala  Glu  Lys  Lys
865                      870                     875                          880

Trp  Arg  Asp  Lys  Arg  Glu  Lys  Leu  Glu  Leu  Glu  Thr  Asn  Ile  Val  Tyr
                    885                     890                          895

Lys  Glu  Ala  Lys  Glu  Ser  Val  Asp  Ala  Leu  Phe  Val  Asn  Ser  Gln  Tyr
               900                     905                     910

Asp  Arg  Leu  Gln  Ala  Asp  Thr  Asn  Ile  Ala  Met  Ile  His  Ala  Ala  Asp
          915                      920                     925

Lys  Arg  Val  His  Ser  Ile  Arg  Glu  Ala  Tyr  Leu  Pro  Glu  Leu  Ser  Val
     930                     935                     940

Ile  Pro  Gly  Val  Asn  Ala  Ala  Ile  Phe  Glu  Glu  Leu  Glu  Gly  Arg  Ile
945                      950                     955                          960

Phe  Thr  Ala  Phe  Ser  Leu  Tyr  Asp  Ala  Arg  Asn  Val  Ile  Lys  Asn  Gly
               965                      970                     975

Asp  Phe  Asn  Tyr  Gly  Leu  Ser  Cys  Trp  Asn  Val  Lys  Gly  His  Val  Asp
               980                     985                     990

Val  Glu  Glu  Gln  Asn  Asn  His  Arg  Ser  Val  Leu  Val  Val  Pro  Glu  Trp
          995                     1000                    1005

Glu  Ala  Glu  Val  Ser  Gln  Glu  Val  Arg  Val  Cys  Pro  Gly  Arg  Gly  Tyr
     1010                    1015                    1020

Ile  Leu  Arg  Val  Thr  Ala  Tyr  Lys  Glu  Gly  Tyr  Gly  Glu  Gly  Cys  Val
1025                     1030                    1035                         1040

Thr  Ile  His  Glu  Ile  Glu  Asn  Asn  Thr  Asp  Glu  Leu  Lys  Phe  Ser  Asn
                    1045                    1050                    1055

Cys  Val  Glu  Glu  Glu  Val  Tyr  Pro  Asn  Asn  Thr  Val  Thr  Cys  Asn  Asp
               1060                    1065                    1070

Tyr  Thr  Ala  Thr  Gln  Glu  Glu  Tyr  Glu  Gly  Thr  Tyr  Thr  Ser  Arg  Asn
               1075                    1080                    1085

Arg  Gly  Tyr  Asp  Gly  Ala  Tyr  Glu  Ser  Asn  Ser  Ser  Val  Pro  Ala  Asp
          1090                    1095                    1100

Tyr  Ala  Ser  Ala  Tyr  Glu  Glu  Lys  Ala  Tyr  Thr  Asp  Gly  Arg  Arg  Asp
1105                     1110                    1115                         1120

Asn  Pro  Cys  Glu  Ser  Asn  Arg  Gly  Tyr  Gly  Asp  Tyr  Thr  Pro  Leu  Pro
                    1125                    1130                    1135

Ala  Gly  Tyr  Val  Thr  Lys  Glu  Leu  Glu  Tyr  Phe  Pro  Glu  Thr  Asp  Lys
          1140                    1145                    1150
```

Val Trp Ile Glu Ile Gly Glu Thr Glu Gly Thr Phe Ile Val Asp Ser
        1155                    1160                1165

Val Glu Leu Leu Leu Met Glu Glu
        1170            1175

(2) INFORMATION FOR SEQ ID NO:3:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (ix) FEATURE:
        (A) NAME/KEY: Region
        (B) LOCATION: 1..133
        (D) OTHER INFORMATION: /note="Sub-Sequence A"

(xi) SEQUENCE DESCRIPTION: SEQ ID NO:3:

Ile Thr Ser Pro Gln Tyr Gly Ile Thr Ala Asn Ala Glu Pro Arg Arg
1               5                   10                  15

Thr Ile Ala Pro Gly Pro Phe Gln Gly Val Pro Ser Leu Leu Tyr Arg
            20                  25                  30

Thr Leu Ser Asp Pro Phe Phe Arg Arg Ser Asp Asn Ile Ser Pro Thr
        35                  40                  45

Leu Gly Ile Asn Val Val Gln Gly Val Gly Phe Leu Gln Pro Asn Asn
        50                  55                  60

Phe Glu Ser Leu Tyr Arg Arg Arg Gly Thr Val Asp Ser Leu Asp Glu
65                  70                  75                  80

Leu Pro Ile Asp Gly Glu Asn Pro Leu Val Gly Tyr Ser His Arg Leu
                85                  90                  95

Ser His Val Thr Leu Thr Arg Ser Leu Phe Asn Thr Asn Ile Thr Ser
            100                 105                 110

Leu Pro Thr Phe Val Trp Thr His His Ser Ala Thr Asp Thr Asn Thr
        115                 120                 125

Ile Ala Pro Asp Val
        130

(2) INFORMATION FOR SEQ ID NO:4:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (ix) FEATURE:
        (A) NAME/KEY: Region
        (B) LOCATION: 1..157
        (D) OTHER INFORMATION: /note="Sub-Sequence B"

(xi) SEQUENCE DESCRIPTION: SEQ ID NO:4:

Ile Thr Gln Ile Pro Leu Val Lys Ala Phe Asn Leu His Ser Gly Ala
1               5                   10                  15

|   |   |   |   |   |   |   |   |   |   |   |   |   |   |   |
|---|---|---|---|---|---|---|---|---|---|---|---|---|---|---|
| Thr | Val | Ala | Arg<br>20 | Gly | Pro | Gly | Phe | Thr<br>25 | Gly | Gly | Asp | Ile | Leu<br>30 | Arg | Arg |
| Thr | Asn | Val<br>35 | Gly | Asn | Phe | Gly | Asp<br>40 | Met | Arg | Val | Asn | Ile<br>45 | Thr | Ala | Pro |
| Leu | Ser<br>50 | Gln | Arg | Tyr | Arg | Val<br>55 | Arg | Ile | Arg | Tyr | Ala<br>60 | Ser | Thr | Thr | Asn |
| Leu<br>65 | Arg | Phe | His | Thr | Ser<br>70 | Ile | Asn | Gly | Arg | Ala<br>75 | Ile | Asn | Gln | Ala | Asp<br>80 |
| Phe | Pro | Ala | Thr | Met<br>85 | Asn | Ser | Gly | Gly | Asn<br>90 | Leu | Gln | Ser | Gly | Ser<br>95 | Phe |
| Arg | Ile | Ala | Gly<br>100 | Phe | Thr | Thr | Pro | Phe<br>105 | Thr | Phe | Ser | Asp | Ala<br>110 | Leu | Ser |
| Thr | Phe | Thr<br>115 | Ile | Gly | Ala | Phe | Gly<br>120 | Phe | Ser | Ser | Gly | Asn<br>125 | Glu | Val | Tyr |
| Ile | Asp<br>130 | Arg | Ile | Glu | Phe | Val<br>135 | Pro | Ala | Glu | Val | Thr<br>140 | Phe | Glu | Ala | Glu |
| Tyr<br>145 | Asp | Leu | Glu | Arg | Ala<br>150 | Gln | Lys | Ala | Val | Asn<br>155 | Ala | Leu |

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..13
        ( D ) OTHER INFORMATION: /note="sequence of a plant
            consensus translation initiator (Clontech)"

( x i ) SEQUENCE DESCRIPTION: SEQ ID NO:5:

GTCGACCATG GTC                                                                         13

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..12
        ( D ) OTHER INFORMATION: /note="sequence of a plant
            consensus translation initiator (Joshi)"

( x i ) SEQUENCE DESCRIPTION: SEQ ID NO:6:

TAAACAATGG CT                                                                         12